(12) United States Patent
Sakamoto et al.

(10) Patent No.: US 8,454,857 B2
(45) Date of Patent: *Jun. 4, 2013

(54) POLYMERIZABLE LIQUID CRYSTAL COMPOUNDS, POLYMERIZABLE LIQUID CRYSTAL COMPOSITIONS, LIQUID CRYSTALLINE POLYMERS AND OPTICALLY ANISOTROPIC MATERIALS

(75) Inventors: Kei Sakamoto, Tokyo (JP); Yasushi Nakano, Yonesawa (JP)

(73) Assignee: Zeon Corporation, Tokyo (JP)

( * ) Notice: Subject to any disclaimer, the term of this patent is extended or adjusted under 35 U.S.C. 154(b) by 146 days.

This patent is subject to a terminal disclaimer.

(21) Appl. No.: 12/997,973

(22) PCT Filed: Jun. 17, 2009

(86) PCT No.: PCT/JP2009/060996
§ 371 (c)(1),
(2), (4) Date: Mar. 2, 2011

(87) PCT Pub. No.: WO2010/001725
PCT Pub. Date: Jan. 7, 2010

(65) Prior Publication Data
US 2011/0140041 A1    Jun. 16, 2011

(30) Foreign Application Priority Data

Jun. 30, 2008 (JP) ................. 2008-170835

(51) Int. Cl.
| C09K 19/52 | (2006.01) |
|---|---|
| C09K 19/06 | (2006.01) |
| C09K 19/00 | (2006.01) |
| C08F 2/00 | (2006.01) |
| C07C 69/74 | (2006.01) |

(52) U.S. Cl.
USPC .......... 252/299.01; 252/299.6; 428/1.1; 428/1.2; 428/1.3; 560/1; 560/8; 560/55; 560/64; 560/73; 526/72; 526/297; 526/298; 526/310; 526/312

(58) Field of Classification Search
USPC .......... 252/299.01, 299.6; 428/1.1, 1.2, 428/1.3; 560/1, 8, 55, 64, 73; 526/72, 297, 526/298, 310, 312
See application file for complete search history.

(56) References Cited

U.S. PATENT DOCUMENTS

| 6,010,642 | A | 1/2000 | Takatsu | |
|---|---|---|---|---|
| 6,136,225 | A | 10/2000 | Meyer | |
| 8,158,021 | B2 * | 4/2012 | Sakamoto et al. | 252/299.01 |
| 2010/0258764 | A1 | 10/2010 | Sakamoto | |

FOREIGN PATENT DOCUMENTS

| JP | 10-147562 | 6/1998 |
|---|---|---|
| JP | 2005-213226 A1 | 8/2005 |
| WO | WO 2008/133290 A1 | 11/2008 |

OTHER PUBLICATIONS

Supplementary European Search Report issued for corresponding European Patent Application No. 09773303 issued on Jun. 22, 2011.
International Search Report for International Application No. PCT/JP2009/060996 dated Sep. 14, 2009.

* cited by examiner

*Primary Examiner* — Geraldina Viscoti
(74) *Attorney, Agent, or Firm* — Kratz, Quintos & Hanson, LLP

(57) ABSTRACT

A polymerizable liquid crystal compound shown by the following formula, a polymerizable liquid crystal composition that includes the polymerizable liquid crystal compound and a chiral compound polymerizable with the polymerizable liquid crystal compound, a liquid crystalline polymer obtained by polymerizing the polymerizable liquid crystal compound or the polymerizable liquid crystal composition, and an optically anisotropic article that includes the liquid crystalline polymer, are disclosed.

$$Z_1 \!-\!\!\!+\!\!Y_1\!-\!G_1\!\!+\!\!_a Y_2\!-\!A_1\!-\!Y_3\!-\!M_1\!-\!\!\underset{L_1\ L_2}{\overset{N=N}{\diagup\!\!\diagdown}}\!\!-\!M_2\!-\!Y_4\!-$$
$$-\!A_2\!-\!Y_5\!\!+\!\!G_2\!-\!Y_6\!\!+\!\!_b Z_2$$

wherein $Y_1$ to $Y_6$ represent —O—C(=O)— or the like, $G_1$ and $G_2$ represent a divalent aliphatic group having 1 to 20 carbon atoms or the like, $Z_1$ and $Z_2$ represent an alkenyl group having 2 to 10 carbon atoms or the like, $A_1$ and $A_2$ represent a divalent organic group having 1 to 30 carbon atoms, $M_1$ and $M_2$ represent a substituted or unsubstituted 2,6-naphthylene group or a substituted or unsubstituted 1,4-phenylene group, provided that at least one of $M_1$ and $M_2$ represents a substituted or unsubstituted 2,6-naphthylene group, $L_1$ and $L_2$ represent a hydrogen atom or the like, and a and b are 0 or 1. A polymerizable liquid crystal compound that shows a liquid crystal phase over a wide temperature range, is chemically stable, can be produced inexpensively, and has a wide selective reflection wavelength band Δλ (i.e., a large value Δn); a polymerizable liquid crystal composition that includes the compound; a liquid crystalline polymer; and a optically anisotropic article that includes the liquid crystalline polymer as a constituting material; can be provided.

23 Claims, No Drawings

POLYMERIZABLE LIQUID CRYSTAL COMPOUNDS, POLYMERIZABLE LIQUID CRYSTAL COMPOSITIONS, LIQUID CRYSTALLINE POLYMERS AND OPTICALLY ANISOTROPIC MATERIALS

TECHNICAL FIELD

The present invention relates to a polymerizable liquid crystal compound, a polymerizable liquid crystal composition that includes the polymerizable liquid crystal compound and a polymerizable chiral compound, a liquid crystalline polymer obtained by polymerizing the polymerizable liquid crystal compound or the polymerizable liquid crystal composition, and an optically anisotropic article that comprises the liquid crystalline polymer as a constituting material.

BACKGROUND ART

In recent years, a liquid crystal alignment film obtained by aligning a liquid crystal polymer or a liquid crystal compound including a polymerizable functional group has been developed as an optical film (e.g., optical compensator) used for liquid crystal displays. Such a liquid crystal alignment film has attracted attention since it is possible to implement a state of high degree of alignment (e.g., tilted alignment or twist alignment) that cannot be implemented by a birefringence film that utilizes polymer film stretching technology.

A cholesteric polarizer that utilizes the selective reflectivity of a liquid crystal alignment film (selective reflection film) obtained by subjecting a composition that includes a liquid crystalline polymer or a polymerizable liquid crystal compound (e.g., (meth)acrylate compound) and a chiral compound to a cholesteric alignment process has also been put to practical use.

The selective reflection center wavelength λ of the selective reflectivity is indicated by "λ=n×P" (where, n is the average refractive index, and P is the cholesteric pitch). The selective reflection wavelength band Δλ is indicated by "Δλ=Δn×P" (where, Δn is (ne−no) (where, ne is the extraordinary refractive index, and no is the ordinary refractive index)). Therefore, a material having a large value Δn (i.e., high optical anisotropy) is required to widen the selective reflection wavelength band Δλ.

When using a selective reflection film for a liquid crystal display as a cholesteric polarizer, the selective reflection film must selectively reflect light in the visible region. Since the selective reflection wavelength band Δλ of a single selective reflection film is normally narrower than the visible region, a plurality of selective reflection films are stacked in order to widen the selective reflection wavelength band Δλ. Specifically, the number of selective reflection films stacked increases when using a material having a narrow selective reflection wavelength band Δλ. As a result, productivity decreases. Therefore, a material (e.g., polymerizable liquid crystal compound) having a large value Δn (i.e., a wide selective reflection wavelength band Δλ) has been desired.

However, since a known polymerizable liquid crystal compound or the like that has a large value Δn exhibits poor solubility, applicability, and alignment properties, it may be impossible to produce a uniform film, or it may be difficult to obtain a selective reflection film that exhibits practical alignment properties.

An azine shown by the following formula (A) has been known as a liquid crystalline compound.

[Chemical Formula 1]

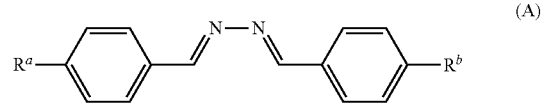

(A)

wherein $R^a$ represents an alkyl group, and $R^b$ represents an alkyl group, a cyano group, a fluorine atom, a trifluoromethoxy group, or the like.

The above azine compound is a liquid crystal material that shows a liquid crystal phase over a wide temperature range, is relatively chemically stable, and can be produced inexpensively, for example.

However, the above azine compound does not necessarily exhibit satisfactory mutual solubility with a liquid crystal compound that is widely used at present. The mutual solubility of the azine compound shown by the formula (A) can be improved by increasing the number of carbon atoms of the side-chain alkyl group. However, the resulting azine compound shows a liquid crystal phase in a narrow temperature range.

In order to solve the above problem, Patent Document 1 discloses a liquid crystal compound shown by the following formula (B).

[Chemical Formula 2]

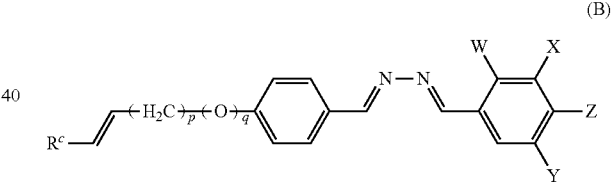

(B)

wherein $R^c$ represents a hydrogen atom or an alkyl group having 1 to 12 carbon atoms (the double bond has a trans configuration when $R^c$ represents an alkyl group), p represents an integer from 1 to 10, q represents 0 or 1, W, X, and Y represent a fluorine atom, a chlorine atom, a methyl group, a cyano group, or a hydrogen atom, and Z represents a fluorine atom, a chlorine atom, a cyano group, an alkyl group or an alkoxy group having 1 to 12 carbon atoms, or an alkenyl group or an alkenyloxy group having 3 to 12 carbon atoms, provided that one or more hydrogen atoms included in these groups may be substituted with a fluorine atom.

The above compound is chemically stable against heat, light, and the like, has excellent liquid crystallinity, and can be easily produced industrially. Since the above compound has excellent mutual solubility with a liquid crystal compound or a liquid crystal composition, the liquid crystal response time can be significantly improved by utilizing the above compound. Therefore, the above compound is considered to be useful as a component of a liquid crystal material for a liquid crystal display element that shows a liquid crystal phase over a wide temperature range and has a quick response time.

However, since an improvement in performance of liquid crystal displays has been increasingly desired, development of a liquid crystal material that shows a liquid crystal phase over a wider temperature range, is chemically stable, can be produced inexpensively, and has a larger value Δn has been desired.

Related-Art Document

Patent Document
Patent Document 1: JP-A-10-147562

DISCLOSURE OF THE INVENTION

Problems to be Solved by the Invention

The present invention was conceived in view of the above problems. An object of the present invention is to provide a polymerizable liquid crystal compound that exhibits excellent mutual solubility with a liquid crystal compound or a liquid crystal composition, shows a liquid crystal phase over a wider temperature range, is chemically stable, can be produced inexpensively, and has a wide selective reflection wavelength band Δλ (i.e., a large value Δn), a polymerizable liquid crystal composition that includes the polymerizable liquid crystal compound, a liquid crystalline polymer obtained by polymerizing the polymerizable liquid crystal compound or the polymerizable liquid crystal composition, and an optically anisotropic article that comprises the liquid crystalline polymer as a constituting material.

Means for Solving the Problems

The inventors of the present invention conducted extensive studies in order to achieve the above object. As a result, the inventors found that a specific polymerizable liquid crystal compound that has an azine skeleton as a conjugated linear atomic group (i.e., a mesogenic group that provides liquid crystal alignment properties) is chemically stable against heat, light, and the like, has excellent mutual solubility with a liquid crystal compound or a liquid crystal composition and excellent liquid crystallinity, can be easily produced industrially, has a wide selective reflection wavelength band Δλ (i.e., a large value Δn), and is suitable as a material for a cholesteric liquid crystal layer. This finding has led to the completion of the present invention.

According to a first aspect of the present invention, there is provided the following polymerizable liquid crystal compound (see (1) to (6)).
(1) A polymerizable liquid crystal compound shown by the following formula (I),

[Chemical Formula 3]

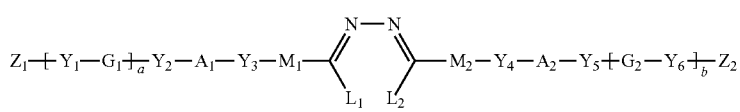

(I)

wherein $Y_1$ to $Y_6$ individually represent a single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—, R$^1$ represents a hydrogen atom or an alkyl group having 1 to 6 carbon atoms, $G_1$ and $G_2$ individually represent a substituted or unsubstituted divalent aliphatic group having 1 to 20 carbon atoms that may include —O—, —S—, —O—C(=O)—, —C(=O)—O—, —O—C(=O)—O—, —NR$^2$—C(=O)—, —C(=O)—NR$^2$—, —NR$^2$—, or —C(=O)— (excluding a case where the divalent aliphatic group includes two or more adjacent —O— or —S—), R$^2$ represents a hydrogen atom or an alkyl group having 1 to 6 carbon atoms, $Z_1$ and $Z_2$ individually represent an alkenyl group having 2 to 10 carbon atoms that may be substituted with a halogen atom, $A_1$ and $A_2$ individually represent a divalent organic group A having 1 to 30 carbon atoms, $M_1$ and $M_2$ individually represent a substituted or unsubstituted 2,6-naphthylene group or a substituted or unsubstituted 1,4-phenylene group, provided that at least one of $M_1$ and $M_2$ represents a substituted or unsubstituted 2,6-naphthylene group, $L_1$ and $L_2$ individually represent a hydrogen atom or an alkyl group having 1 to 6 carbon atoms, and a and b are individually 0 or 1.

(2) The polymerizable liquid crystal compound according to (1), wherein $A_1$ and $A_2$ individually represent a substituted or unsubstituted phenylene group, a substituted or unsubstituted biphenylene group, or a substituted or unsubstituted naphthylene group.

(3) The polymerizable liquid crystal compound according to (1) or (2), wherein $Z_1$ and $Z_2$ individually represent CH$_2$=CH—, CH$_2$=C(CH$_3$)—, CH$_2$=CH—CH$_2$—, CH$_3$—CH=CH—, CH$_2$=CH—CH$_2$—CH$_2$—, CH$_2$=C(CH$_3$)—CH$_2$—CH$_2$—, (CH$_3$)$_2$C=CH—CH$_2$—, (CH$_3$)$_2$C=CH—CH$_2$—CH$_2$—, CH$_2$=C(Cl)—, CH$_2$=C(CH$_3$)—CH$_2$—, or CH$_3$—CH=CH—CH$_2$—.

(4) The polymerizable liquid crystal compound according to any one of (1) to (3), wherein $M_1$ represents a substituted or unsubstituted 2,6-naphthylene group, and $M_2$ represents a substituted or unsubstituted 1,4-phenylene group.

(5) The polymerizable liquid crystal compound according to (1), wherein $Y_1$ to $Y_6$ individually represent —O—, —C(=O)—O—, or —O—C(=O)—, $G_1$ and $G_2$ individually represent —(CH$_2$)$_6$— or —(CH$_2$)$_4$— that may include —O—, —C(=O)—O—, or —O—C(=O)—, $Z_1$ and $Z_2$ individually represent CH$_2$=CH—, CH$_2$=C(CH$_3$)—, or CH$_2$=C(Cl)—, $A_1$ and $A_2$ individually represent one of the groups shown by the following formulas,

[Chemical Formula 4]

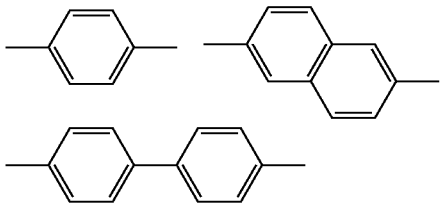

M₁ represents a substituted or unsubstituted 2,6-naphthylene group, and M₂ represents a substituted or unsubstituted 1,4-phenylene group.

(6) The polymerizable liquid crystal compound according to (1), wherein $Y_1$ to $Y_6$ individually represent —O—, —C(=O)—O—, or —O—C(=O)—, $G_1$ and $G_2$ individually represent —(CH₂)₆— or —(CH₂)₄—, $Z_1$ and $Z_2$ individually represent CH₂=CH— or CH₂=C(CH₃)—, $A_1$ and $A_2$ represent the group shown by the following formula,

[Chemical Formula 5]

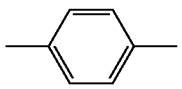

M₁ represents a substituted or unsubstituted 2,6-naphthylene group, and M₂ represents a substituted or unsubstituted 1,4-phenylene group.

(7) The polymerizable liquid crystal compound according to (1), wherein $Y_1$ to $Y_6$ individually represent —O—, —C(=O)—O—, or —O—C(=O)—, $G_1$ and $G_2$ individually represent —(CH₂)₆— or —(CH₂)₄—, $Z_1$ and $Z_2$ represent CH₂=CH—, $A_1$ and $A_2$ represent the group shown by the following formula,

[Chemical Formula 6]

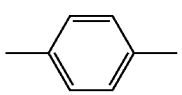

M₁ represents a 2,6-naphthylene group, and M₂ represents a substituted or unsubstituted 1,4-phenylene group.

(8) The polymerizable liquid crystal compound according to (1), wherein $L_1$ and $L_2$ represent a hydrogen atom.

According to a second aspect of the present invention, there is provided the following polymerizable liquid crystal composition (see (9)).

(9) A polymerizable liquid crystal composition including the polymerizable liquid crystal compound according to any one of (1) to (8), and a polymerizable chiral compound that is polymerizable with the polymerizable liquid crystal compound.

According to a third aspect of the present invention, there is provided the following liquid crystal polymer (see (10)).

(10) A liquid crystalline polymer obtained by polymerizing the polymerizable liquid crystal compound according to any one of (1) to (8) or the polymerizable liquid crystal composition according to (9).

According to a fourth aspect of the present invention, there is provided the following optically anisotropic article (see (11)).

(11) An optically anisotropic article comprising the liquid crystalline polymer according to (10) as a constituting material.

Effects of the Invention

The above polymerizable liquid crystal compound is a liquid crystal material of a liquid crystalline polymer that shows a liquid crystal phase over a wide temperature range, is chemically stable, can be produced inexpensively, and has a wide selective reflection wavelength band Δλ (i.e., high optical anisotropy (Δn)).

The above polymerizable liquid crystal composition enables formation of a liquid crystal layer that shows a liquid crystal phase over a wide temperature range and has a wide selective reflection wavelength band Δλ (i.e., a large value Δn).

The above liquid crystal polymer has excellent alignment properties and a large value Δn.

Since the above optically anisotropic article is produced using the above polymerizable liquid crystal compound, the optically anisotropic article exhibits uniform and high-quality liquid crystal alignment properties.

DESCRIPTION OF EXEMPLARY EMBODIMENTS

1) The polymerizable liquid crystal compound, 2) the polymerizable liquid crystal composition, 3) the liquid crystal polymer, and 4) the optically anisotropic article according to the present invention are described in detail below.

1) Polymerizable Liquid Crystal Compound

A polymerizable liquid crystal compound of the present invention is a compound shown by the formula (I).

$Y_1$ to $Y_6$ in the formula (I) individually represent a single bond, —O—, —S—, —O—C(=O)—, —C(=O)—O—, —O—C(=O)—O—, —NR¹—C(=O)—, —C(=O)—NR¹—, —O—C(=O)—NR¹—, —NR¹—C(=O)—O—, —NR¹—C(=O)—NR¹—, —O—NR¹—, or —NR¹—O—. Among these, —O—, —O—C(=O)—, and —C(=O)—O— are preferable.

$R^1$ represents a hydrogen atom or an alkyl group having 1 to 6 carbon atoms, such as a methyl group, an ethyl group, an n-propyl group, an isopropyl group, an n-butyl group, an isobutyl group, a sec-butyl group, a t-butyl group, an n-pentyl group, an isopentyl group, a neopentyl group, or an n-hexyl group. $R^1$ preferably represents a hydrogen atom or a methyl group.

It is preferable that $Y_1$ and $Y_3$ be —C(=O)—O—, $Y_4$ and $Y_6$ be —O—C(=O)—, and $Y_2$ and $Y_5$ be —O—, or $Y_1$ to $Y_3$ be —C(=O)—O— and $Y_4$ to $Y_6$ be —O—C(=O)—, so that the polymerizable liquid crystal compound can be easily synthesized, and advantageously exhibits the desired effects.

$G_1$ and $G_2$ individually represent a substituted or unsubstituted divalent aliphatic group having 1 to 20 carbon atoms, and preferably a divalent aliphatic group having 1 to 12 carbon atoms.

Examples of the divalent aliphatic group having 1 to 20 carbon atoms represented by $G_1$ and $G_2$ include chain-like aliphatic groups, aliphatic groups having an alicyclic structure, and the like. The divalent aliphatic group represented by $G_1$ and $G_2$ is preferably a chain-like aliphatic group (e.g., an alkylene group having 1 to 20 carbon atoms or an alkenylene group having 2 to 20 carbon atoms), more preferably an alkylene group having 1 to 12 carbon atoms (e.g., methylene group, ethylene group, trimethylene group, propylene group, tetramethylene group, pentamethylene group, hexamethylene group, or octamethylene group), and particularly preferably a tetramethylene group (—$(CH_2)_4$—) or a hexamethylene group (—$(CH_2)_6$—), so that the polymerizable liquid crystal compound advantageously exhibits the desired effects.

Examples of a substituent for the divalent aliphatic group represented by $G_1$ and $G_2$ include halogen atoms such as a fluorine atom, a chlorine atom, a bromine atom, and an iodine atom; alkoxy groups having 1 to 6 carbon atoms, such as a methoxy group, an ethoxy group, an n-propoxy group, an isopropoxy group, an n-butoxy group, a sec-butoxy group, a t-butoxy group, an n-pentyloxy group, and an n-hexyloxy group; and the like. Among these, a fluorine atom, a methoxy group, and an ethoxy group are preferable.

Note that the aliphatic group may include —O—, —S—, —O—C(=O)—, —C(=O)—O—, —O—C(=O)—O—, —$NR^2$—C(=O)—, —C(=O)—$NR^2$—, —$NR^2$—, or —C(=O)— (excluding a case where the aliphatic group includes two or more adjacent —O— or —S—). Among these, —O—, —O—C(=O)—, and —C(=O)—O— are preferable.

$R^2$ represents a hydrogen atom or an alkyl group having 1 to 6 carbon atoms similar to that represented by $R^1$, and preferably a hydrogen atom or a methyl group.

Specific examples of the aliphatic group that may include the above group include —$CH_2$—$CH_2$—O—$CH_2$—$CH_2$—, —$CH_2$—$CH_2$—S—$CH_2$—$CH_2$—, —$CH_2$—$CH_2$—O—C(=O)—$CH_2$—$CH_2$—, —$CH_2$—$CH_2$—C(=O)—O—$CH_2$—, —$CH_2$—O—C(=O)—O—$CH_2$—$CH_2$—, —$CH_2$—$CH_2$—$NR^2$—C(=O)—$CH_2$—$CH_2$—, —$CH_2$—$CH_2$—C(=O)—$NR^2$—$CH_2$—, —$CH_2$—$NR^2$—$CH_2$—$CH_2$—, —$CH_2$—C(=O)—$CH_2$—, and the like.

$Z_1$ and $Z_2$ individually represent an alkenyl group having 2 to 10 carbon atoms that may be substituted with a halogen atom.

The alkenyl group having 2 to 10 carbon atoms represented by $Z_1$ and $Z_2$ is preferably an alkenyl group having 2 to 6 carbon atoms.

Examples of the halogen atom that may substitute the alkenyl group include a fluorine atom, a chlorine atom, a bromine atom, and the like. Among these, a chlorine atom is preferable.

Specific examples of the alkenyl group having 2 to 10 carbon atoms represented by $Z_1$ and $Z_2$ that may be substituted with a halogen atom include $CH_2$=CH—, $CH_2$=C($CH_3$)—, $CH_2$=CH—$CH_2$—, $CH_3$—CH=CH—, $CH_2$=CH—$CH_2$—$CH_2$—, $CH_2$=C($CH_3$)—$CH_2$—$CH_2$—, $(CH_3)_2$C=CH—$CH_2$—, $(CH_3)_2$C=CH—$CH_2$—$CH_2$—, $CH_2$=C(Cl)—, $CH_2$=C($CH_3$)—$CH_2$—, $CH_3$—CH=CH—$CH_2$—, and the like.

Among these, the alkenyl group represented by $Z_1$ and $Z_2$ is preferably $CH_2$=CH—, $CH_2$=C($CH_3$)—, $CH_2$=C(Cl)—, $CH_2$=CH—$CH_2$—, $CH_2$=C($CH_3$)—$CH_2$—, or $CH_2$=C($CH_3$)—$CH_2$—$CH_2$—, more preferably $CH_2$=CH—, $CH_2$=C($CH_3$)—, or $CH_2$=C(Cl)—, still more preferably $CH_2$=CH— or $CH_2$=C($CH_3$)—, and particularly preferably $CH_2$=CH—, so that the polymerizable liquid crystal compound advantageously exhibits the desired effects.

Specific examples of the groups shown by —$Y_2$-($G_1$-$Y_1$)$_a$—$Z_1$ and —$Y_5$-($G_2$-$Y_6$)$_b$—$Z_2$ bonded to $A_1$ and $A_2$ are given below. Note that a and b respectively indicate the number of ($G_1$-$Y_1$) units and the number of ($G_2$-$Y_6$) units, and are individually 0 or 1. It is preferable that a or b be 1, and it is more preferable that a and b be 1, so that the polymerizable liquid crystal compound can be easily synthesized, and advantageously exhibits the desired effects.

When a or b is 1, the group shown by —$Y_2$-($G_1$-$Y_1$)$_a$—$Z_1$ or —$Y_5$-($G_2$-$Y_6$)$_b$—$Z_2$ has a structure shown by the following formula (C).

[Chemical Formula 7]

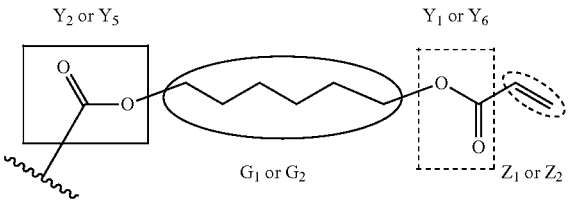

(C)

wherein $Y_2$ or $Y_5$ represents —C(=O)—O—, $G_1$ or $G_2$ represents a hexamethylene group, $Y_1$ or $Y_6$ represents —O—C(=O)—, and $Z_1$ or $Z_2$ represents a vinyl group.

Specific examples of the structure shown by the formula (C) are given below.

[Chemical Formula 8]

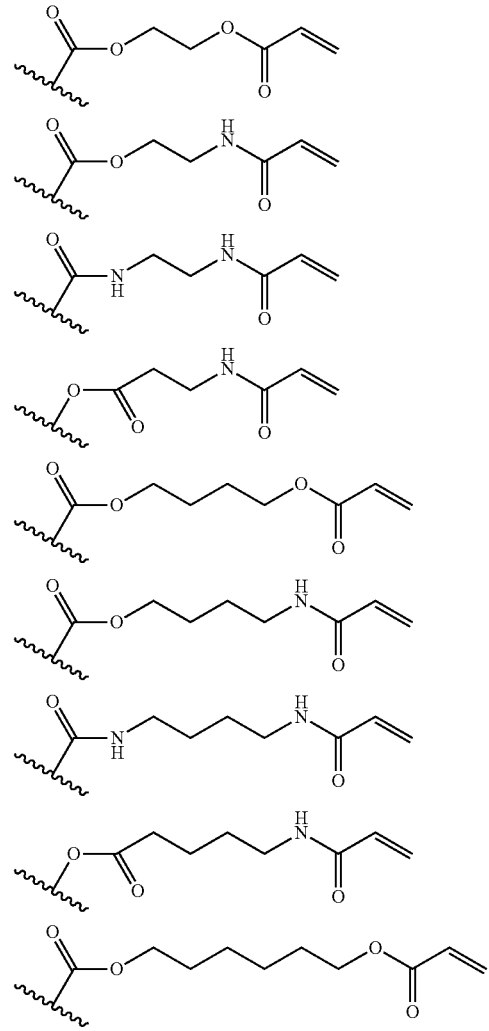

[Chemical Formula 9]
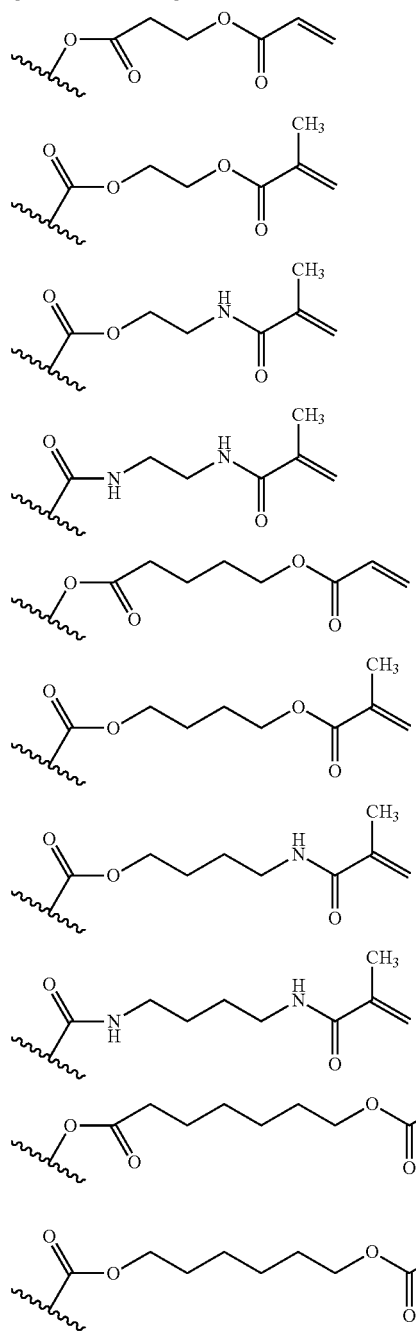
[Chemical Formula 10]
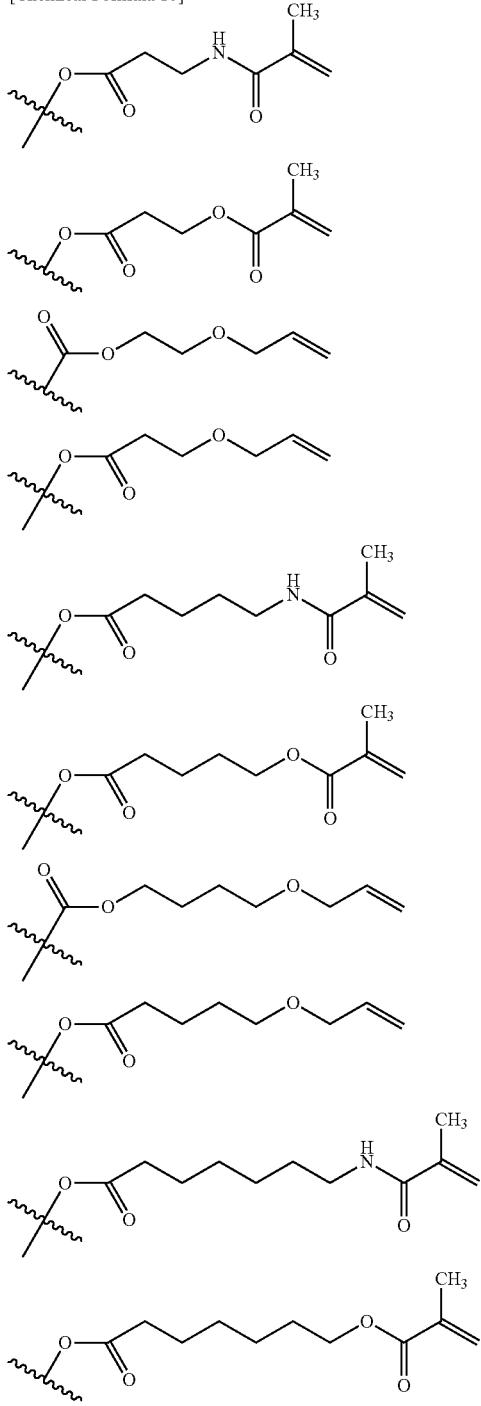

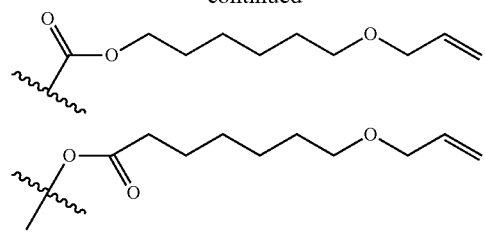
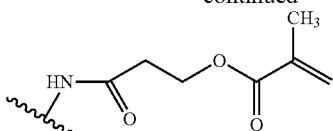
[Chemical Formula 11]
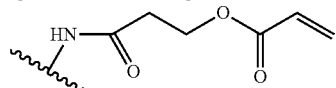
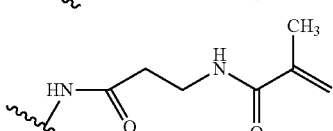
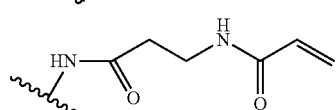
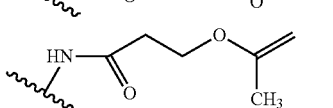
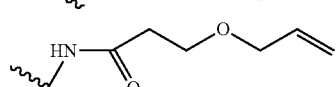
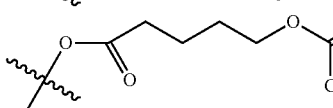
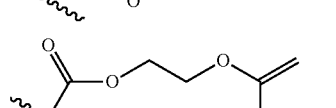
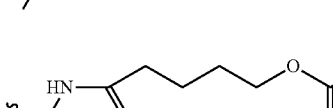
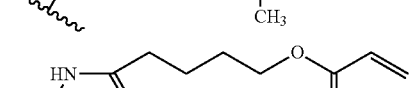
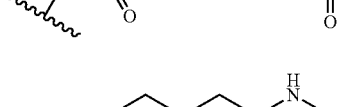
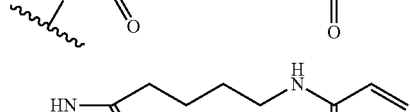
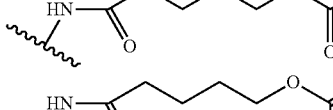
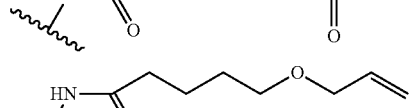
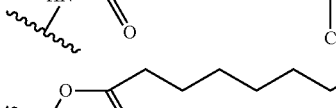
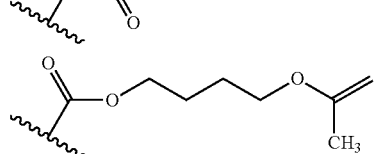
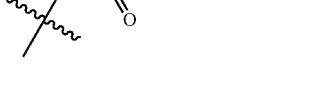
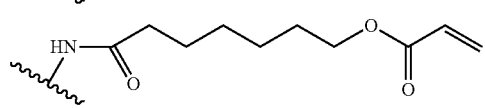
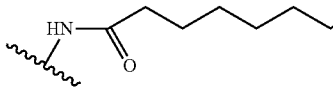
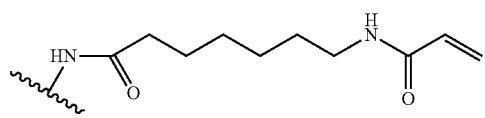
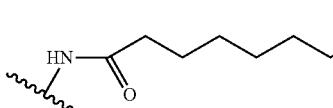
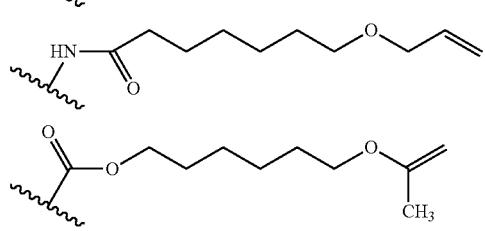
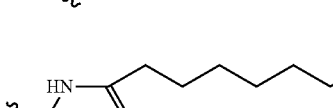
[Chemical Formula 12]
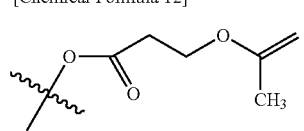
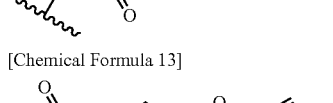
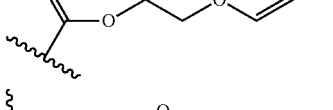
[Chemical Formula 13]
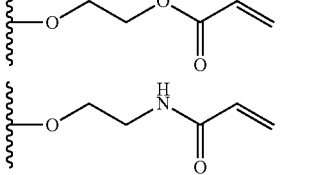

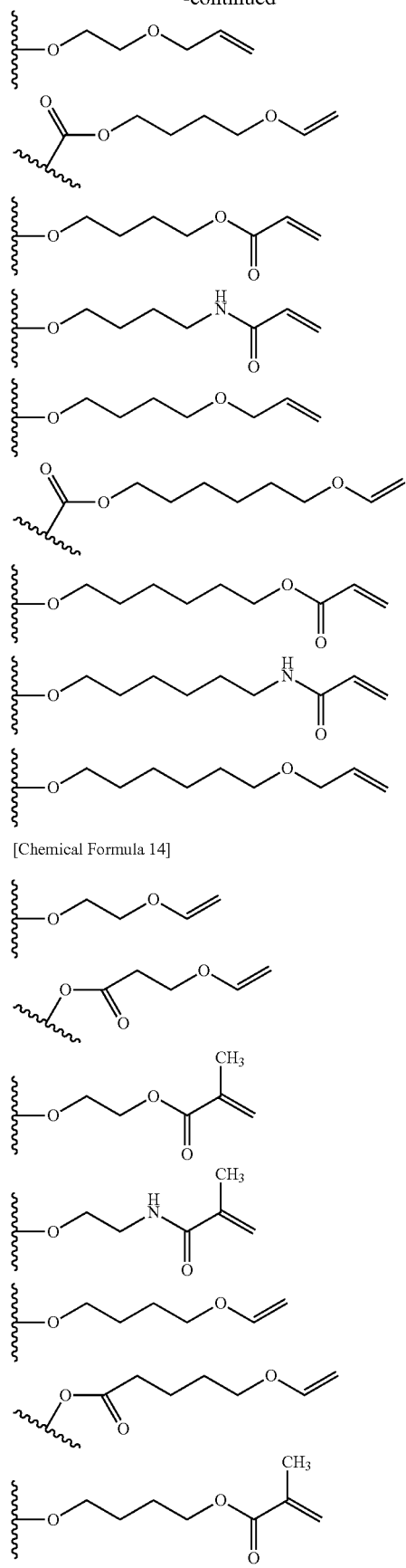
[Chemical Formula 14]
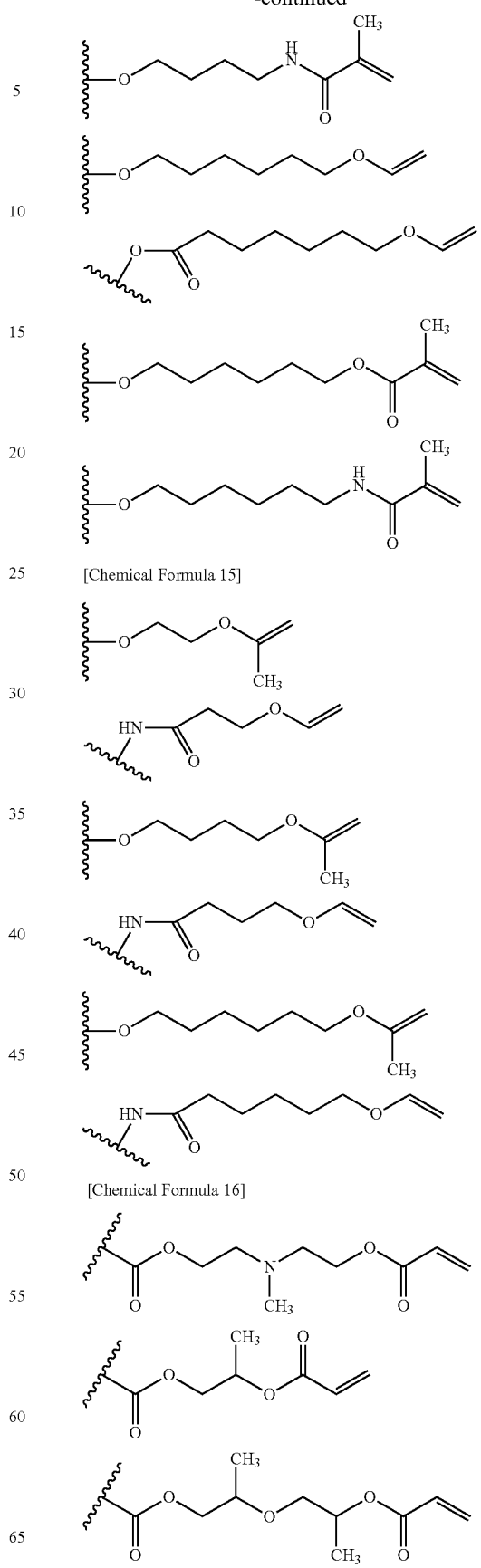
[Chemical Formula 15]
[Chemical Formula 16]

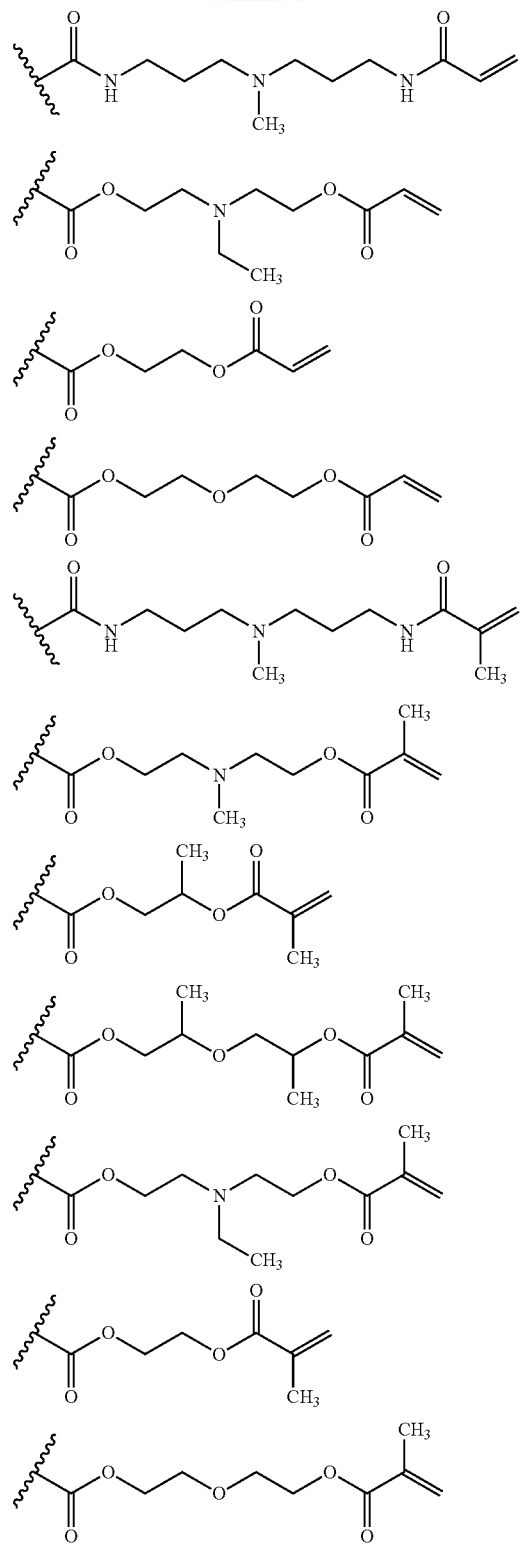
[Chemical Formula 17]
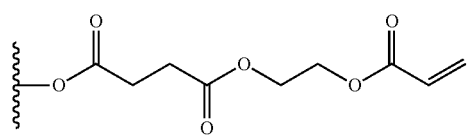
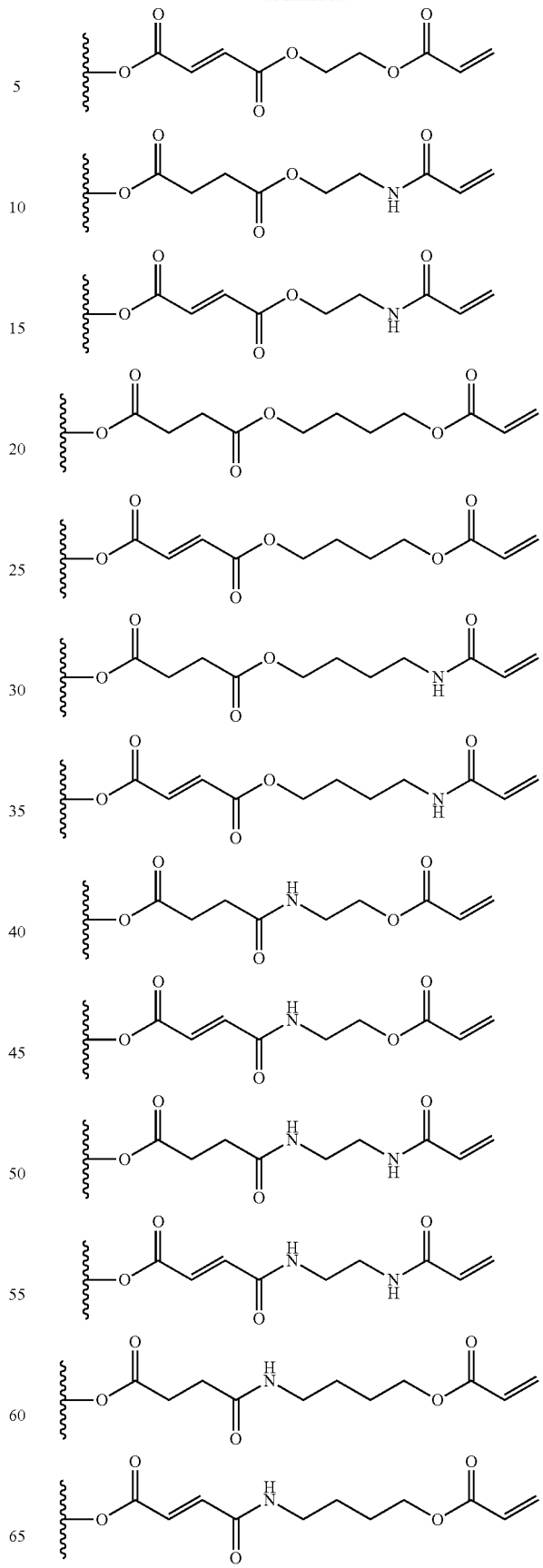

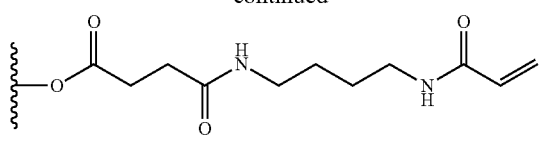
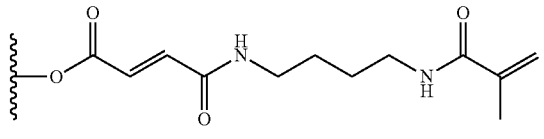
[Chemical Formula 18]
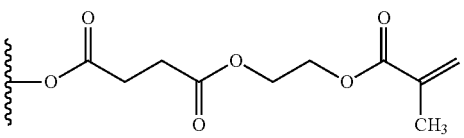
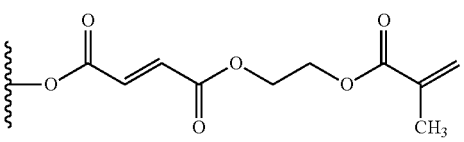
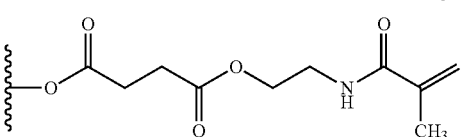
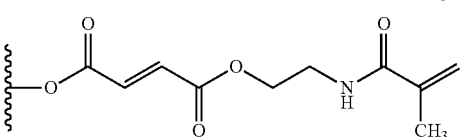
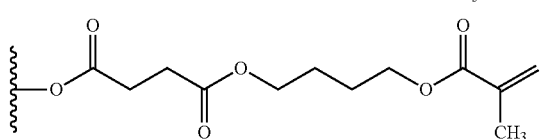
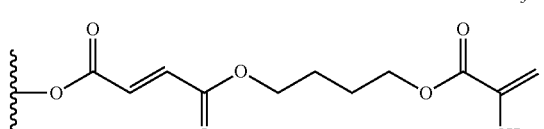
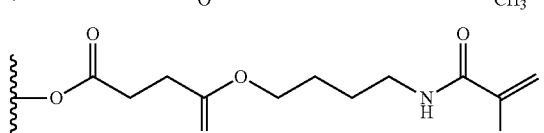
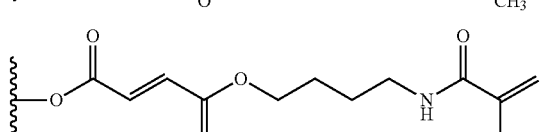
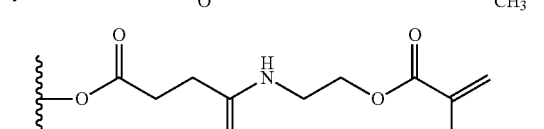
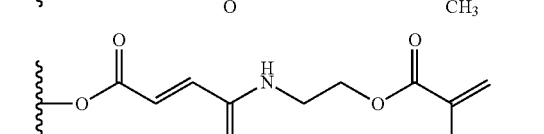
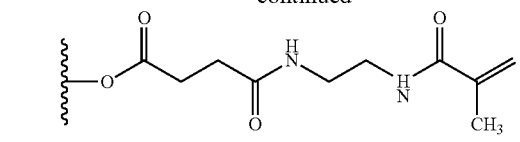
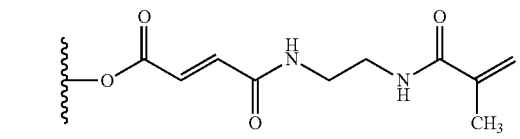
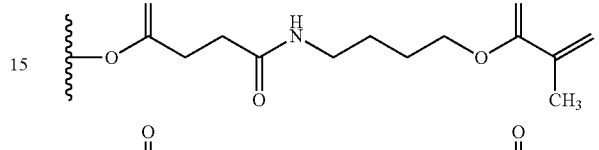
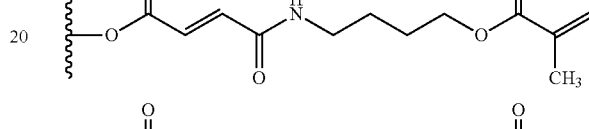
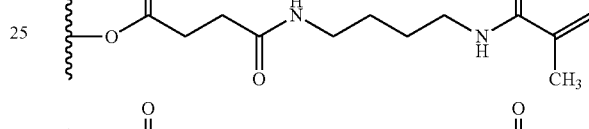
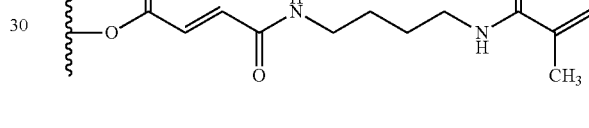
When a or b is 0, the group shown by —Y$_2$-(G$_1$-Y$_1$)$_a$—Z$_1$ or —Y$_5$-(G$_2$-Y$_6$)$_b$—Z$_2$ has a structure shown by the following formula (D).
[Chemical Formula 19]
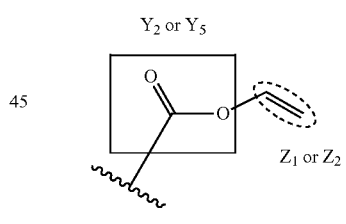
(D)
wherein Y$_2$ or Y$_5$ represents —C(=O)—O—, and Z$_1$ or Z$_2$ represents a vinyl group.
Specific examples of the structure shown by the formula (D) are given below.
[Chemical Formula 20]
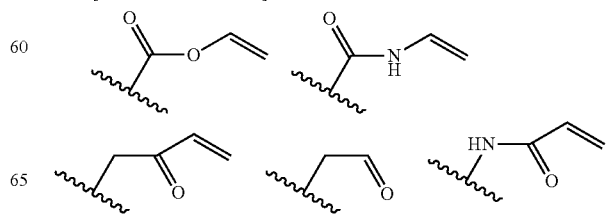

-continued

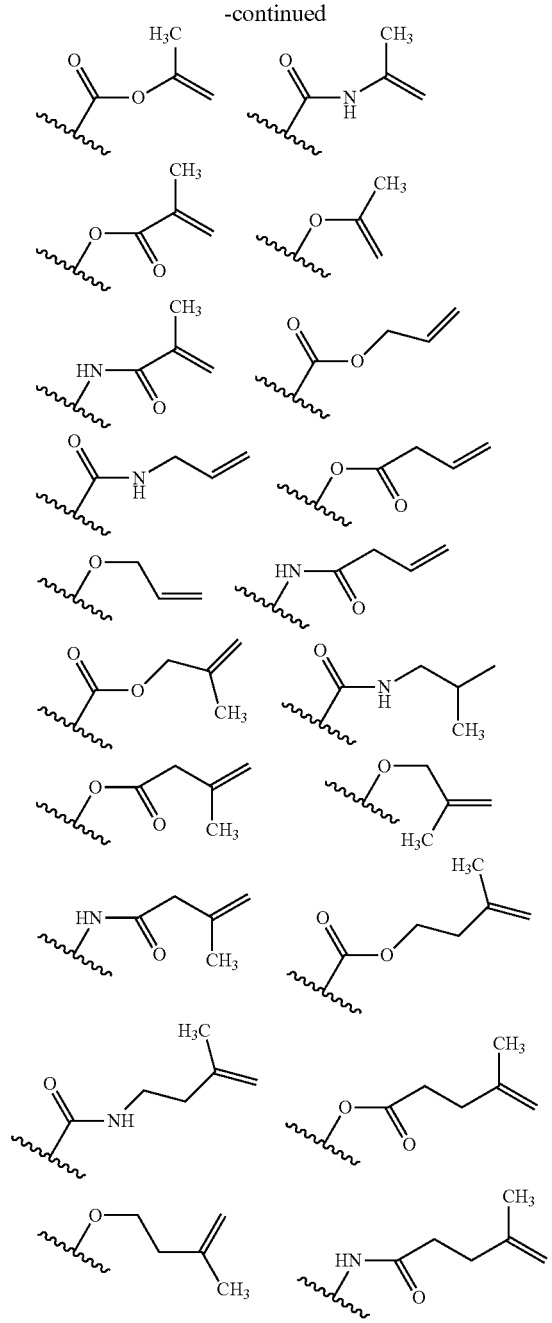

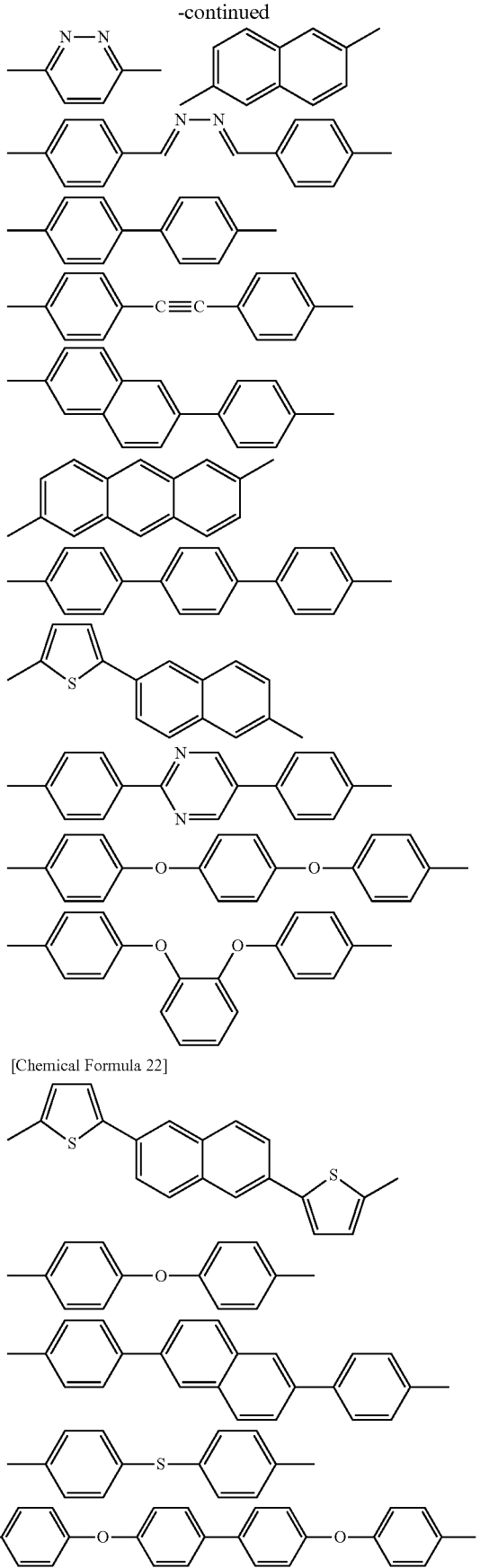

A$_1$ and A$_2$ individually represent a divalent organic group A having 1 to 30 carbon atoms. The number of carbon atoms of the organic group A is preferably 6 to 20. The organic group A represented by A$_1$ and A$_2$ is not particularly limited, but preferably has an aromatic ring.

Specific examples of the organic group represented by A$_1$ and A$_2$ are given below.

[Chemical Formula 21]

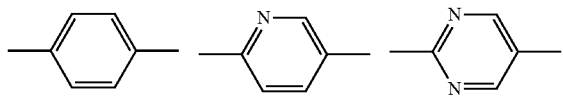

[Chemical Formula 22]

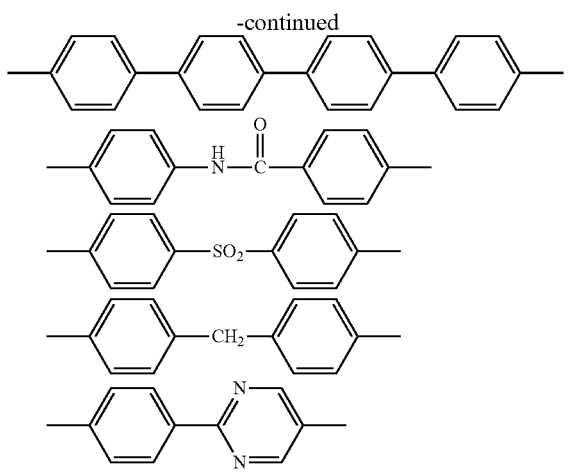

The organic groups represented by $A_1$ and $A_2$ may have a plurality of identical or different substituents at arbitrary positions.

Examples of the substituents include halogen atoms such as a fluorine atom and a chlorine atom; a cyano group; a hydroxyl group; alkyl groups having 1 to 6 carbon atoms, such as a methyl group and an ethyl group; alkoxy groups having 1 to 6 carbon atoms, such as a methoxy group and an ethoxy group; a nitro group; —C(=O)—OR; and the like. Note that R represents an alkyl group having 1 to 6 carbon atoms, such as a methyl group or an ethyl group, or a substituted or unsubstituted phenyl group such as a phenyl group and a 4-methylphenyl group.

Among these, a halogen atom, an alkyl group having 1 to 6 carbon atoms, and an alkoxy group having 1 to 6 carbon atoms are preferable, and a fluorine atom, a methyl group, an ethyl group, a propyl group, a methoxy group, and an ethoxy group are more preferable.

$A_1$ and $A_2$ preferably represent a substituted or unsubstituted phenylene group, a substituted or unsubstituted biphenylene group, or a substituted or unsubstituted naphthylene group, more preferably a group shown by the following formula $(A_{11})$, $(A_{21})$, or $(A_{31})$ that may have a substituent, and particularly preferably the group shown by the following formula $(A_{11})$ that may have a substituent, so that the polymerizable liquid crystal compound advantageously exhibits the desired effects.

[Chemical Formula 23]

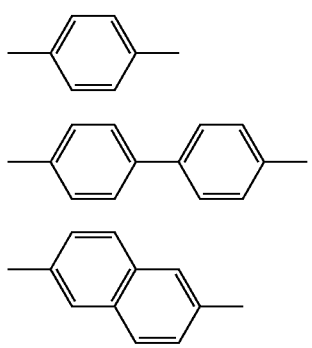

In the polymerizable liquid crystal compound shown by the formula (I), the groups shown by the following formulas may be the same or different.

$Z_1\text{-}[Y_1\text{-}G_1]_a\text{-}Y_2\text{-}A_1\text{-}Y_3\text{—}$ [Chemical Formula 24]

$\text{—}Y_4\text{-}A_2\text{-}Y_5\text{-}[G_2\text{-}Y_6]_b\text{-}Z_2$ [Chemical Formula 25]

$M_1$ and $M_2$ individually represent a substituted or unsubstituted 2,6-naphthylene group or a substituted or unsubstituted 1,4-phenylene group, provided that at least one of $M_1$ and $M_2$ represents a substituted or unsubstituted 2,6-naphthylene group.

Specifically, (i) both $M_1$ and $M_2$ represent a substituted or unsubstituted 2,6-naphthylene group, or (ii) either $M_1$ or $M_2$ represents a substituted or unsubstituted 2,6-naphthylene group, and the other represents a substituted or unsubstituted 1,4-phenylene group. It is preferable that (ii) either $M_1$ or $M_2$ represent a substituted or unsubstituted 2,6-naphthylene group, and the other represent a substituted or unsubstituted 1,4-phenylene group, so that the polymerizable liquid crystal compound advantageously exhibits the desired effects.

Examples of a substituent for a substituted or unsubstituted 2,6-naphthylene group and a substituted or unsubstituted 1,4-phenylene group include a halogen atom, a substituted or unsubstituted alkyl group having 1 to 10 carbon atoms, a cyano group, a nitro group, —$OR^3$, —O—C(=O)—$R^3$, —C(=O)—$OR^3$, —O—C(=O)—$OR^3$, —$NR^4$—C(=O)—$R^3$, —C(=O)—$NR^3$, —O—C(=O)—$NR^3$, —$Y_7$-$G_3$-$Y_8$—$Z_3$, and the like.

Among these, a halogen atom, a substituted or unsubstituted alkyl group having 1 to 10 carbon atoms, —$OR^3$, —O—C(=O)—$R^3$, —C(=O)—$OR^3$, and —O—C(=O)—$OR^3$ are preferable, and a substituted or unsubstituted alkyl group having 1 to 10 carbon atoms, —$OR^3$, and —C(=O)—$OR^3$ are more preferable.

$R^3$ represents a hydrogen atom or a substituted or unsubstituted alkyl group having 1 to 10 carbon atoms. Examples of the alkyl group having 1 to 10 carbon atoms include a methyl group, an ethyl group, an n-propyl group, an isopropyl group, an n-butyl group, a sec-butyl group, a t-butyl group, an n-pentyl group, an n-hexyl group, and the like. Among these, an alkyl group having 1 to 4 carbon atoms, such as a methyl group, an ethyl group, an n-propyl group, an isopropyl group, or an n-butyl group is preferable.

Examples of a substituent for the substituted or unsubstituted alkyl group having 1 to 10 carbon atoms represented by $R^3$ include halogen atoms such as a fluorine atom, a chlorine atom, a bromine atom, and an iodine atom; alkoxy groups having 1 to 6 carbon atoms, such as a methoxy group, an ethoxy group, an n-propoxy group, an isopropoxy group, an n-butoxy group, a sec-butoxy group, a t-butoxy group, an n-pentyloxy group, and an n-hexyloxy group; and the like.

When $R^3$ represents an alkyl group, the alkyl group may include —O—, —S—, —O—C(=O)—, —C(=O)—O—, —O—C(=O)—O—, —$NR^5$—C(=O)—, —C(=O)—$NR^5$—, —$NR^5$—, or —C(=O)—. Among these, —O—, —O—C(=O)—, and —C(=O)—O— are preferable.

Note that a case where the alkyl group includes two or more adjacent —O— or —S— is excluded.

$R^4$ and $R^5$ individually represent a hydrogen atom or an alkyl group having 1 to 6 carbon atoms (e.g., methyl group or ethyl group).

Specific examples of the alkyl group that is represented by $R^3$ and includes —O—, —S—, —O—C(=O)—, —C(=O)—O—, —O—C(=O)—O—, —$NR^5$—C(=O)—, —C(=O)—$NR^5$—, —$NR^5$—, or —C(=O)— include —$CH_2$—$CH_2$—O—$CH_2$—$CH_3$, —$CH_2$—$CH_2$—S—$CH_2$—$CH_3$, —$CH_2$—$CH_2$—O—C(=O)—$CH_3$, —$CH_2$—$CH_2$—C(=O)—O—$CH_3$, —$CH_2$—O—C(=O)—O—$CH_2$—$CH_3$, —$CH_2$—$CH_2$—$NR^2$—C(=O)—

$CH_3$, $-CH_2-CH_2-C(=O)-NR^2-CH_3$, $-CH_2-NR^2-CH_2-CH_3$, $-CH_2-CH_2-C(=O)-CH_3$, and the like.

$Y_7$ and $Y_8$ have the same meaning as $Y_1$ to $Y_6$, $G_3$ has the same meaning as $G_1$ and $G_2$, and $Z_3$ has the same meaning as $Z_1$ and $Z_2$.

Specific examples of the group shown by $-Y_7-G_3-Y_8-Z_3$ include the groups shown by $-Y_2-(G_1-Y_1)_a-Z_1$ and $-Y_5-(G_2-Y_6)_b-Z_2$ in which a and b are 1.

The substituted or unsubstituted 2,6-naphthylene group is preferably a 2,6-naphthylene group from the viewpoint of availability of the raw material and production of the desired polymerizable liquid crystal compound.

The substituted or unsubstituted 1,4-phenylene group is preferably (1) a 1,4-phenylene group, (2) a 1,4-phenylene group to which $-OCH_3$, $-OCH_2CH_3$, or $-CH_3$ is bonded at positions 3 and 5 (the carbon atom of the 1,4-phenylene group that is bonded to the azine skeleton is referred to as position 1; hereinafter the same), (3) a 1,4-phenylene group to which $-C(=O)-OCH_3$, $-C(=O)-OCH_2CH_3$, $-C(=O)-OCH_2CH_2CH_3$, $-C(=O)-O-CH_2CH_2OCH_2CH_2CH_3$, $-C(=O)-OCH_2CH_2CH_2CH_3$, $-OCH_3$, $-OCH_2CH_3$, $-CH_3$, $-CH_2CH_3$, $-CH_2CH_2CH_3$, or a fluorine atom is bonded at position 3, or (4) a 1,4-phenylene group to which $-C(=O)-OCH_3$, $-C(=O)-OCH_2CH_3$, $-C(=O)-OCH_2CH_2CH_3$, $-C(O)-O-CH_2CH_2OCH_2CH_2CH_3$, $-C(=O)-OCH_2CH_2CH_2CH_3$, $-OCH_3$, $-OCH_2CH_3$, $-CH_3$, $-CH_2CH_3$, $-CH_2CH_2CH_3$, or a fluorine atom is bonded at position 2.

The substituted or unsubstituted 1,4-phenylene group is more preferably (1a) a 1,4-phenylene group, (2a) a 1,4-phenylene group to which $-OCH_3$ is bonded at positions 3 and 5, or (3a) a 1,4-phenylene group to which $-C(=O)-OCH_3$, $-C(=O)-O-CH_2CH_2OCH_2CH_2CH_3$, $-C(=O)-O-CH_2CH_2CH_3$, or $-O-CH_2CH_3$ is bonded at position 3.

The polymerizable liquid crystal compound is preferably (α) a compound shown by the formula (I) wherein $Y_1$ to $Y_6$ individually represent $-O-$, $-C(=O)-O-$, or $-O-C(=O)-$, $G_1$ and $G_2$ individually represent $-(CH_2)_6-$ or $-(CH_2)_4-$ that may include $-O-$, $-C(=O)-O-$, or $-O-C(=O)-$, $Z_1$ and $Z_2$ individually represent $CH_2=CH-$, $CH_2=C(CH_3)-$, or $CH_2=C(Cl)-$, $A_1$ and $A_2$ individually represent one of the groups shown by the following formulas,

[Chemical Formula 26]

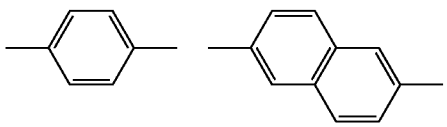

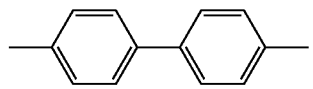

$M_1$ represents a substituted or unsubstituted 2,6-naphthylene group, and $M_2$ represents a substituted or unsubstituted 1,4-phenylene group, more preferably (β) a compound shown by the formula (I) wherein $Y_1$ to $Y_6$ individually represent $-O-$, $-C(=O)-O-$, or $-O-C(=O)-$, $G_1$ and $G_2$ individually represent $-(CH_2)_6-$ or $-(CH_2)_4-$, $Z_1$ and $Z_2$ individually represent $CH_2=CH-$ or $CH_2=C(CH_3)-$, $A_1$ and $A_2$ represent the group shown by the following formula,

[Chemical Formula 27]

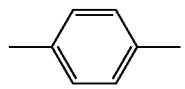

$M_1$ represents a substituted or unsubstituted 2,6-naphthylene group, and $M_2$ represents a substituted or unsubstituted 1,4-phenylene group, and still more preferably (γ) a compound shown by the formula (I) wherein $Y_1$ to $Y_6$ individually represent $-O-$, $-C(=O)-O-$, or $-O-C(=O)-$, $G_1$ and $G_2$ individually represent $-(CH_2)_6-$ or $-(CH_2)_4-$, $Z_1$ and $Z_2$ represent $CH_2=CH-$, $A_1$ and $A_2$ represent the group shown by the following formula,

[Chemical Formula 28]

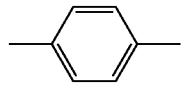

$M_1$ represents a 2,6-naphthylene group, and $M_2$ represents a substituted or unsubstituted 1,4-phenylene group.

$L_1$ and $L_2$ individually represent a hydrogen atom or an alkyl group having 1 to 6 carbon atoms. $L_1$ and $L_2$ preferably represent a hydrogen atom or a methyl group, and more preferably represent a hydrogen atom.

Specific examples of a preferable polymerizable liquid crystal compound shown by the formula (I) are given below.

[Chemical Formula 29]

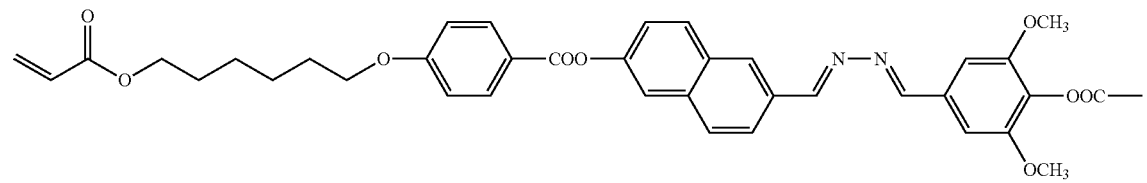

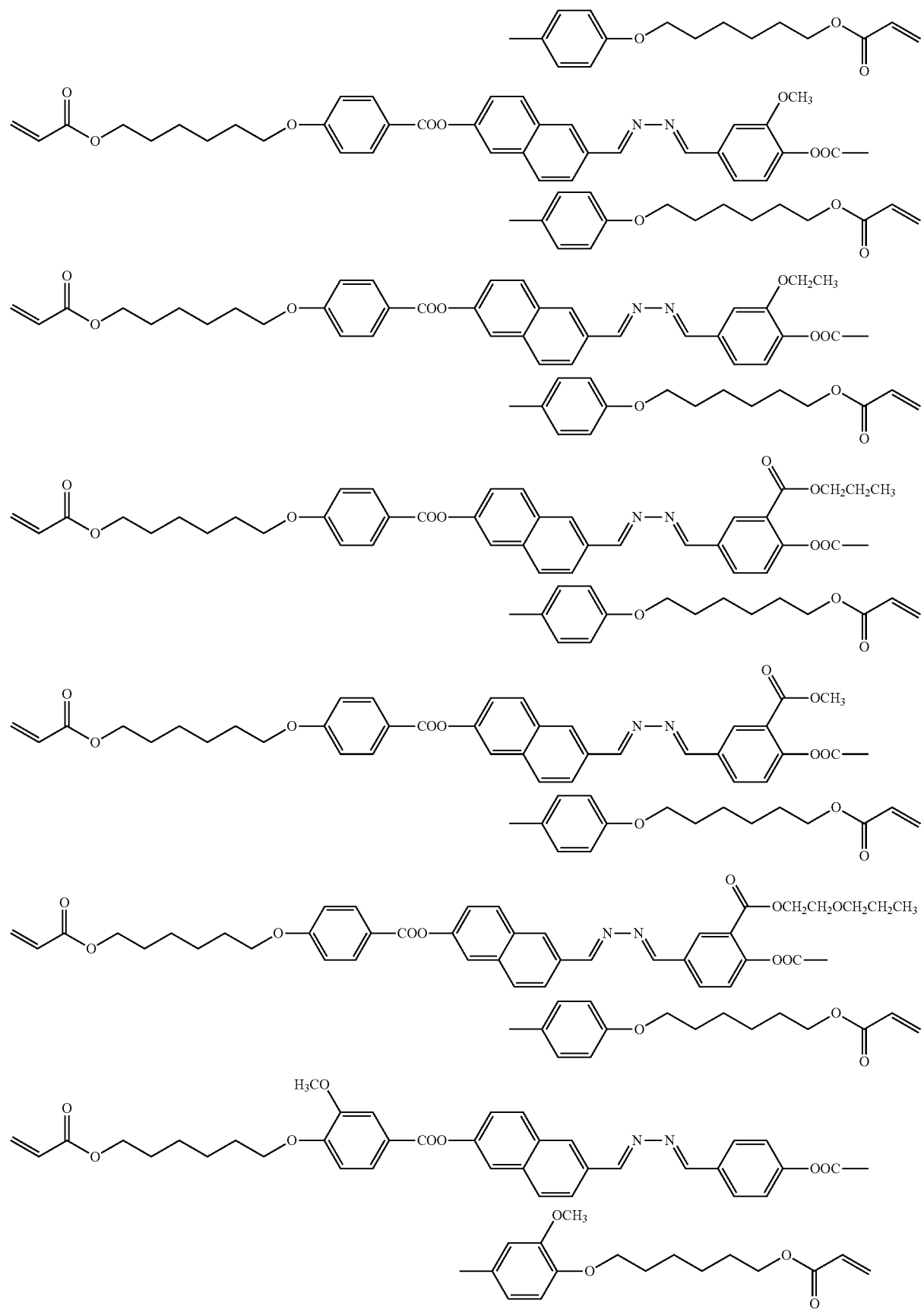

-continued
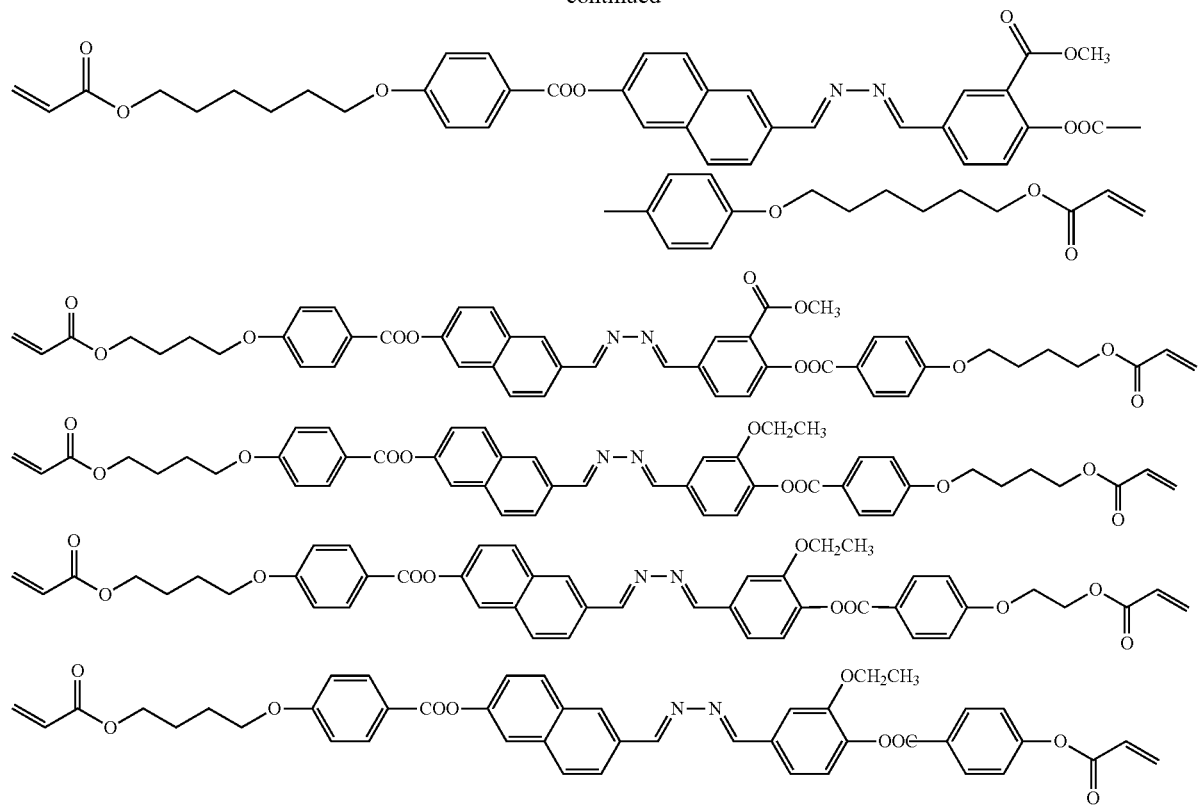
[Chemical Formula 30]
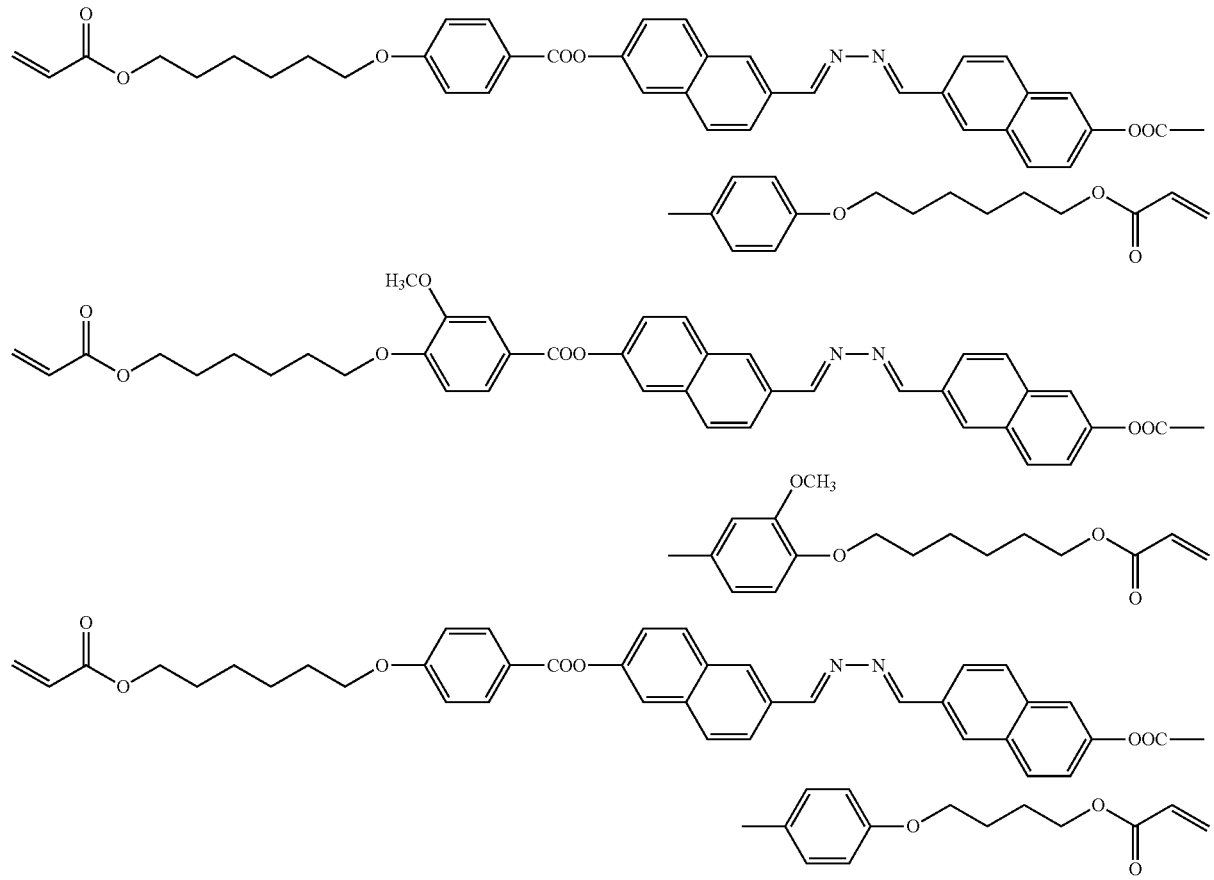

-continued

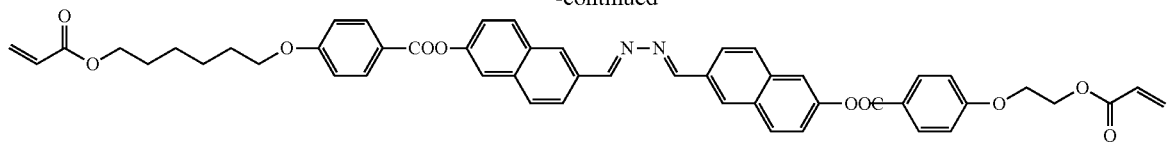

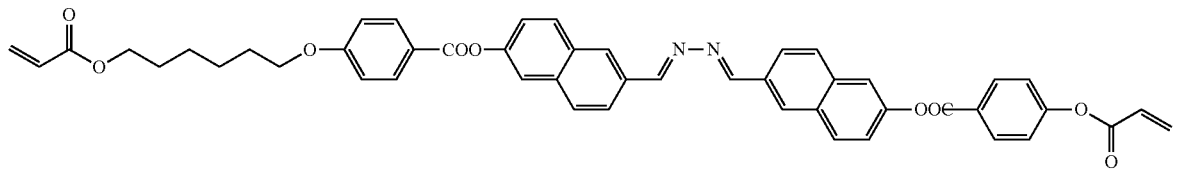

The above polymerizable liquid crystal compound may be prepared by combining known methods that form various chemical bonds (e.g., —O—, —S—, —NH—C(=O)—, —C(=O)NH—, —NHC(=O)NH—, —O—C(=O)—, or —C(=O)—O—) (refer to Sandler and Karo, Organic Functional Group Preparations [I] and [II], Hirokawa Publishing, 1976, for example).

The polymerizable liquid crystal compound may be prepared by appropriately bonding and modifying a plurality of known compounds having a desired structure by arbitrarily combining an ether bond (—O—)-forming reaction, an ester bond (—C(=O)—O—)-forming reaction, an amide bond (—C(=O)NH—)-forming reaction, and an acid chloride (—COCl)-forming reaction.

An ether bond may be formed as follows, for example.

(i) A compound shown by Q1-X (wherein X represents a halogen atom; hereinafter the same) and a compound shown by Q2-OM (wherein M represents an alkali metal atom (mainly a sodium atom); hereinafter the same) are mixed and condensed. Note that Q1 and Q2 represent an arbitrary organic group B (hereinafter the same). This reaction is generally referred to as Williamson synthesis.

(ii) A compound shown by Q1-X and a compound shown by Q2-OH are mixed and condensed in the presence of a base (e.g., sodium hydroxide or potassium hydroxide).

(iii) A compound shown by Q1-E (wherein E represents an epoxy group) and a compound shown by Q2-OH are mixed and condensed in the presence of a base (e.g., sodium hydroxide or potassium hydroxide).

(iv) A compound shown by Q1-OFN (wherein OFN represents a group that includes an unsaturated bond) and a compound shown by Q2-OM are mixed and subjected to an addition reaction in the presence of a base (e.g., sodium hydroxide or potassium hydroxide).

(v) A compound shown by Q1-X and a compound shown by Q2-OM are mixed and condensed in the presence of copper or cuprous chloride. This reaction is generally referred to as Ullmann condensation.

An ester bond and an amide bond may be formed as follows, for example.

(i) A compound shown by Q1-COOH and a compound shown by Q2-OH or Q2-NH$_2$ are subjected to dehydration/condensation in the presence of a dehydration/condensation agent (e.g., N,N-dicyclohexylcarbodiimide).

(ii) A compound shown by Q1-COOH is reacted with a halogenating agent to obtain a compound shown by Q1-COX, and the compound shown by Q1-COX and a compound shown by Q2-OH or Q2-NH$_2$ are reacted in the presence of a base.

(iii) A compound shown by Q1-COOH is reacted with an acid anhydride to obtain a mixed acid anhydride, and the mixed acid anhydride is reacted with a compound shown by Q2-OH or Q2-NH$_2$.

(iv) A compound shown by Q1-COOH and a compound shown by Q2-OH or Q2-NH$_2$ are subjected to dehydration/condensation in the presence of an acid catalyst or a base catalyst.

An acid chloride may be formed as follows, for example.

(i) A compound shown by Q1-COOH is reacted with phosphorus trichloride or phosphorus pentachloride.

(ii) A compound shown by Q1-COOH is reacted with thionyl chloride.

(iii) A compound shown by Q1-COOH is reacted with oxalyl chloride.

(iv) A compound shown by Q1-COOAg is reacted with chlorine or bromine.

(v) A compound shown by Q1-COOH is reacted with a carbon tetrachloride solution of red mercuric oxide.

When synthesizing the polymerizable liquid crystal compound, the yield can be improved by protecting a hydroxyl group of an intermediate. A hydroxyl group may be protected by a known method (refer to Greene's Protective Groups in Organic Synthesis, 3rd version: Wiley-Interscience, 1999, for example).

A hydroxyl group may be protected as follows, for example.

(i) A compound shown by Q1Q2Q3-Si—X and a compound shown by Q4-OH are reacted in the presence of a base (e.g., imidazole or pyridine). Note that Q3 and Q4 represent an arbitrary organic group B (hereinafter the same).

(ii) A vinyl ether (e.g., 3,4-dihydro-2H-pyran) and a compound shown by Q2-OH are reacted in the presence of an acid (e.g., p-toluenesulfonic acid, p-toluenesulfonic acid pyridine salt, or hydrogen chloride).

(iii) A compound shown by Q1-C(=O)—X and a compound shown by Q4-OH are reacted in the presence of a base (e.g., triethylamine or pyridine).

(iv) An acid anhydride compound shown by Q1-C(=O)—O—C(=O)-Q2 and a compound shown by Q3-OH are reacted optionally in the presence of a base (e.g., sodium hydroxide or triethylamine).

(v) A compound shown by Q1-X and a compound shown by Q2-OH are reacted in the presence of a base (e.g., sodium hydroxide or triethylamine).
(vi) A compound shown by Q1-O—CH$_2$—X and a compound shown by Q2-OH are reacted in the presence of a base (e.g., sodium hydride, sodium hydroxide, triethylamine, or pyridine).
(vii) A compound shown by Q1-O—CH$_2$—C(=O)—X and a compound shown by Q4-OH are reacted in the presence of a base (e.g., potassium carbonate or sodium hydroxide).
(viii) A compound shown by Q1-O—C(=O)—X and a compound shown by Q2-OH are reacted in the presence of a base (e.g., triethylamine or pyridine).

A hydroxyl group may be deprotected by the following methods, for example.
(i) A hydroxyl group is deprotected by mixing with a fluoride (e.g., tetrabutylammonium fluoride).
(ii) A hydroxyl group is deprotected with mixing in the presence of an acid (e.g., p-toluenesulfonic acid, p-toluenesulfonic acid pyridine salt, hydrogen chloride, or acetic acid).
(iii) A hydroxyl group is deprotected with mixing in the presence of a base (e.g., sodium hydride, sodium hydroxide, potassium hydroxide, sodium carbonate, potassium carbonate, triethylamine, or pyridine).
(iv) A hydroxyl group is deprotected by hydrogenation in the presence of a hydrogenation catalyst (e.g., Pd—C).

These methods may be appropriately used depending on the structure and the type of protecting group.

The target product may be isolated by performing a post-treatment operation normally employed in organic chemistry after completion of the reaction, followed by a known purification/separation means such as column chromatography, recrystallization, or distillation, as required.

The structure of the target product may be identified by measurement, elementary analysis, or the like (e.g., NMR spectrum, IR spectrum, or mass spectrum).

2) Polymerizable Liquid Crystal Composition

A polymerizable liquid crystal composition of the present invention includes the above polymerizable liquid crystal compound, and a polymerizable chiral compound that is polymerizable with the polymerizable liquid crystal compound.

The polymerizable liquid crystal composition of the present invention includes one or more types of the above polymerizable liquid crystal compounds as an essential component. The composition of the present invention may include a known polymerizable liquid crystal compound disclosed in JP-A-11-130729, JP-A-8-104870, JP-A-2005-309255, JP-A-2005-263789, JP-A-2002-533742, JP-A-2002-308832, JP-A-2002-265421, JP-A-62-070406, JP-A-11-100575, or the like (hereinafter may be referred to as "additional polymerizable liquid crystal compound") in addition to the above polymerizable liquid crystal compound.

The content of the additional polymerizable liquid crystal compound in the composition of the present invention is not particularly limited, but is preferably 50 wt % or less, and more preferably 30 wt % or less, based on the total amount of the polymerizable liquid crystal compounds.

The polymerizable chiral compound included in the composition of the present invention is not particularly limited insofar as the polymerizable chiral compound has an asymmetric carbon in the molecule, is polymerizable with the polymerizable liquid crystal compound, and does not adversely affect the alignment of the polymerizable liquid crystal compound.

The term "polymerization" used herein refers to a chemical reaction in a broad sense including a normal polymerization reaction and a crosslinking reaction.

The composition of the present invention may include only one type of polymerizable chiral compound, or may include two or more types of polymerizable chiral compounds.

The polymerizable liquid crystal compound included in the composition of the present invention forms a cholesteric phase when mixed with the polymerizable chiral compound.

As the polymerizable chiral compound, a known polymerizable chiral compound such as a polymerizable chiral compound disclosed in JP-A-11-193287 may be used. Examples of the polymerizable chiral compound include compounds shown by the following general formulas, and the like. Note that the polymerizable chiral compound is not limited to the compounds shown by the following general formulas.

[Chemical Formula 31]

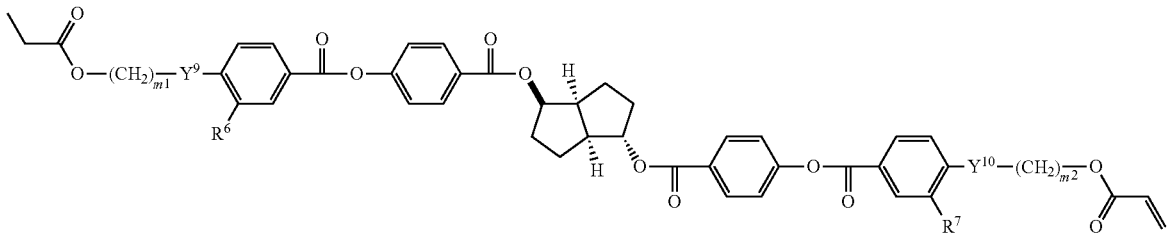

[Chemical Formula 32]

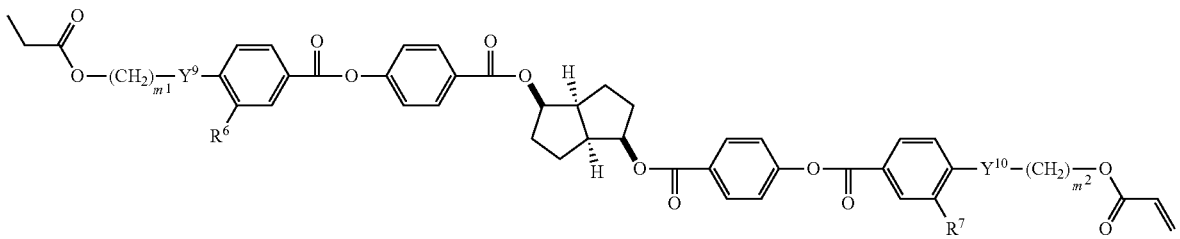

[Chemical Formula 33]

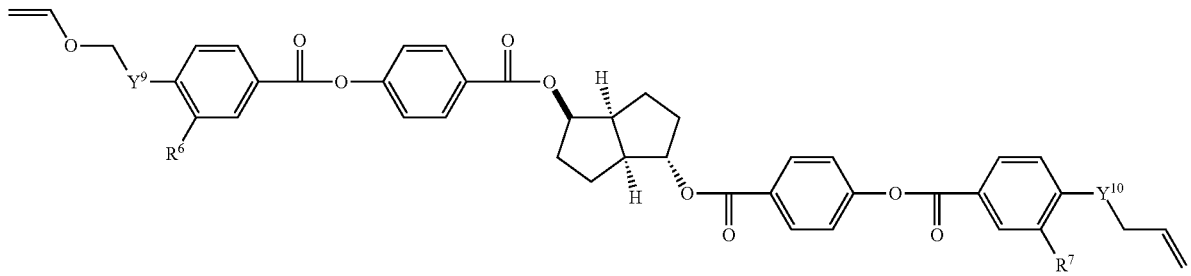

wherein $R^6$ and $R^7$ represent a hydrogen atom, a methyl group, a methoxy group, or the like, $Y^9$ and $Y^{10}$ represent —O—, —O—C(=O)—, —O—C(=O)—O—, or the like, and $m^1$ and $m^2$ are individually 2, 4, or 6.

Specific examples of the compounds shown by the above general formulas include the following compounds.

[Chemical Formula 34]

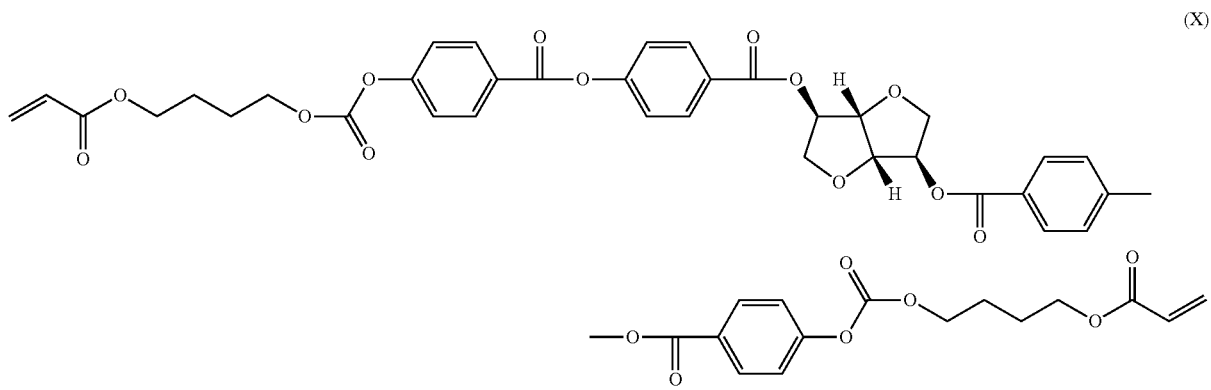

(X)

[Chemical Formula 35]

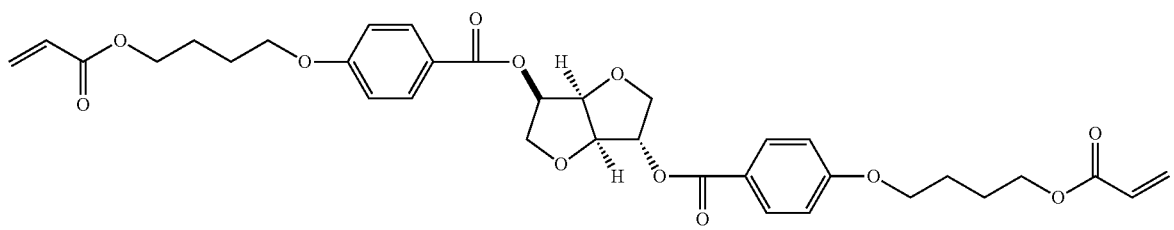

The polymerizable chiral compound is used in the composition of the present invention in an amount of 0.1 to 100 parts by weight, and preferably 0.5 to 10 parts by weight, based on 100 parts by weight of the polymerizable liquid crystal compound.

The composition of the present invention preferably includes a polymerization initiator from the viewpoint of ensuring an efficient polymerization reaction. Examples of the polymerization initiator include polymerization initiators described later in the section entitled "3) Liquid crystalline polymer". The polymerization initiator is used in the composition of the present invention in an amount of 0.1 to 30 parts by weight, and preferably 0.5 to 10 parts by weight, based on 100 parts by weight of the polymerizable liquid crystal compound.

The composition of the present invention preferably includes a surfactant in order to adjust the surface tension of the composition. The surfactant is not particularly limited, but is preferably a nonionic surfactant. Examples of the nonionic surfactant include a nonionic surfactant that is an oligomer having a molecular weight of about several thousand, such as "KH-40" (manufactured by AGC Seimi Chemical Co., Ltd.). The surfactant is used in the composition of the present invention in an amount of 0.01 to 10 parts by weight, and preferably 0.1 to 2 parts by weight, based on 100 parts by weight of the polymerizable liquid crystal compound.

When using the composition of the present invention as a raw material for a polarizing film or an alignment film, a printing ink, a paint, a protective film, or the like, additives such as other copolymerizable monomers, a metal, a metal complex, a dye, a pigment, a fluorescent material, a phosphorescent material, a leveling agent, a thixotropic agent, a gelling agent, a polysaccharide, a UV absorber, an IR (infrared) absorber, an antioxidant, an ion-exchange resin, or a metal oxide (e.g., titanium oxide) may be added to the composition in addition to the above components. Each additive is used in the composition of the present invention in an amount of 0.1 to 20 parts by weight based on 100 parts by weight of the polymerizable liquid crystal compound.

The composition of the present invention may be produced by dissolving given amounts of the polymerizable liquid crystal compound, the polymerizable chiral compound, a photo-initiator, a nonionic surfactant, and optional additives in an appropriate solvent.

Examples of the solvent include ketones such as cyclopentanone, cyclohexanone, and methyl ethyl ketone; esters such as butyl acetate and amyl acetate; halogenated hydrocarbons such as chloroform, dichloromethane, and dichloroethane; ethers such as 1,2-dimethoxyethane, 1,4-dioxane, cyclopentyl methyl ether, tetrahydrofuran, and tetrahydropyran; and the like.

The composition of the present invention thus obtained is useful as a raw material for a cholesteric liquid crystal layer or a cholesteric liquid crystalline polymer (described later).

3) Liquid Crystalline Polymer

A liquid crystalline polymer of the present invention is obtained by polymerizing the polymerizable liquid crystal compound of the present invention or the polymerizable liquid crystal composition of the present invention.

The term "polymerization" used herein refers to a chemical reaction in a broad sense including a normal polymerization reaction and a crosslinking reaction.

The liquid crystalline polymer of the present invention is (1) a liquid crystalline polymer obtained by polymerizing the polymerizable liquid crystal compound of the present invention, or (2) a liquid crystalline polymer obtained by polymerizing the polymerizable liquid crystal composition of the present invention.

(1) Liquid Crystalline Polymer Obtained by Polymerizing the Polymerizable Liquid Crystal Compound of the Present Invention Examples of the liquid crystal polymer obtained by polymerizing the polymerizable liquid crystal compound of the present invention include a homopolymer of the polymerizable liquid crystal compound of the present invention, a copolymer of two or more types of the polymerizable liquid crystal compound of the present invention, a copolymer of the polymerizable liquid crystal compound of the present invention and another polymerizable liquid crystal compound, a copolymer of the polymerizable liquid crystal compound of the present invention and a monomer that is copolymerizable with the polymerizable liquid crystal compound of the present invention, and the like.

Examples of the monomer that is copolymerizable with the polymerizable liquid crystal compound include, but are not limited to, 4'-methoxyphenyl 4-(2-methacryloyloxyethyloxy)benzoate, biphenyl 4-(6-methacryloyloxyhexyloxy)benzoate, 4'-cyanobiphenyl 4-(2-acryloyloxyethyloxy)benzoate, 4'-cyanobiphenyl 4-(2-methacryloyloxyethyloxy)benzoate, 3',4'-difluorophenyl 4-(2-methacryloyloxyethyloxy)benzoate, naphthyl 4-(2-methacryloyloxyethyloxy)benzoate, 4-acryloyloxy-4'-decylbiphenyl, 4-acryloyloxy-4'-cyanobiphenyl, 4-(2-acryloyloxyethyloxy)-4'-cyanobiphenyl, 4-(2-methacryloyloxyethyloxy)-4'-methoxybiphenyl, 4-(2-methacryloyloxyethyloxy)-4'-(4"-fluorobenzyloxy)-biphenyl, 4-acryloyloxy-4'-propylcyclohexylphenyl, 4-methacryloyl-4'-butylbicyclohexyl, 4-acryloyl-4'-amylotolan, 4-acryloyl-4'-(3,4-difluorophenyl)bicyclohexyl, (4-amylphenyl) 4-(2-acryloyloxyethyl)benzoate, [4-(4'-propylcyclohexyl)phenyl]4-(2-acryloyloxyethyl)benzoate, and the like.

When the liquid crystal polymer is a copolymer of the polymerizable liquid crystal compound of the present invention and another polymerizable liquid crystal compound, or a copolymer of the polymerizable liquid crystal compound of the present invention and a monomer that is copolymerizable with the polymerizable liquid crystal compound of the present invention, the content of units derived from the polymerizable liquid crystal compound of the present invention is not particularly limited, but is preferably 50 wt % or more, and more preferably 70 wt % or more, based on the amount of the total units. If the content of the units derived from the polymerizable liquid crystal compound of the present invention is within the above range, a liquid crystalline polymer that has a high glass transition temperature (Tg) and high hardness can be obtained.

The polymerizable liquid crystal compound of the present invention may be polymerized or copolymerized with another polymerizable liquid crystal compound or a monomer that is copolymerizable with the polymerizable liquid crystal compound (hereinafter may be referred to as "copolymerizable monomer or the like") in the presence of an appropriate polymerization initiator. The polymerization initiator is used in an amount similar to that of the polymerization initiator used in the polymerizable liquid crystal composition.

The polymerization initiator may be appropriately selected depending on the type of polymerizable group included in the polymerizable liquid crystal compound. For example, a radical polymerization initiator may be used when the polymerizable group is a radically polymerizable group. An anionic polymerization initiator may be used when the polymerizable group is an anionically polymerizable group. A cationic polymerization initiator may be used when the polymerizable group is a cationically polymerizable group.

As the radical polymerization initiator, a thermal radical generator or a photo-radical generator may be used. It is preferable to use a photo-radical generator.

Examples of the photo-radical generator include benzoins such as benzoin, benzoin methyl ether, and benzoin propyl ether; acetophenones such as acetophenone, 2,2-dimethoxy-2-phenylacetophenone, 2,2-diethoxy-2-phenylacetophenone, 1,1-dichloroacetophenone, 1-hydroxycyclohexyl phenyl ketone, 2-methyl-1-[4-(methylthio)phenyl]-2-morpholino-propan-1-one, and N,N-dimethylaminoacetophenone; anthraquinones such as 2-methylanthraquinone, 1-chloroanthraquinone, and 2-amylanthraquinone; thioxanethones such as 2,4-dimethylthioxanethone, 2,4-diethylthioxanthone, 2-chlorothioxanthone, and 2,4-diisopropylthioxanethone; ketals such as acetophenone dimethyl ketal and benzyl dimethyl ketal; benzophenones such as benzophenone, methylbenzophenone, 4,4-dichlorobenzophenone, 4,4-bisdiethylaminobenzophenone, Michler's ketone, and 4-benzoyl-4-methyldiphenyl sulfide; 2,4,6-trimethylbenzoyldiphenylphosphine oxide; and the like.

Specific examples of the photo-radical polymerization initiator include Irgacure 907, Irgacure 184, Irgacure 369, Irgacure 651 (manufactured by Ciba Specialty Chemicals, Co., Ltd.), and the like.

Examples of the anionic polymerization initiator include alkyllithium compounds; monolithium salts or monosodium salts of biphenyl, naphthalene, pyrene, and the like; polyfunctional initiators such as dilithium and trilithium salts; and the like.

Examples of the cationic polymerization initiator include proton acids such as sulfuric acid, phosphoric acid, perchloric acid, and trifluoromethanesulfonic acid; Lewis acids such as boron trifluoride, aluminum chloride, titanium tetrachloride, and tin tetrachloride; an aromatic onium salt or a combination of an aromatic onium salt and a reducing agent; and the like.

These polymerization initiators may be used either individually or in combination.

The polymerizable liquid crystal compound may be polymerized or copolymerized with the copolymerizable monomer or the like in the presence of a functional compound such as a UV absorber, an IR absorber, or an antioxidant.

The liquid crystalline polymer of the present invention may be produced by (A) polymerizing the polymerizable liquid crystal compound or copolymerizing the polymerizable liquid crystal compound with the copolymerizable monomer or the like in an appropriate organic solvent, or (B) applying a solution prepared by dissolving the polymerizable liquid crystal compound or the polymerizable liquid crystal compound and the copolymerizable monomer or the like in an organic solvent to a support by a known coating method, removing the solvent in a state in which the monomers are aligned, and applying heat or activated energy rays to the resulting film.

The organic solvent used for the method (A) is not particularly limited insofar as the organic solvent is inert. Examples of the organic solvent used for the method (A) include aromatic hydrocarbons such as toluene, xylene, and mesitylene; ketones such as cyclohexanone, cyclopentanone, and methyl ethyl ketone; acetates such as butyl acetate and amyl acetate; halogenated hydrocarbons such as chloroform, dichloromethane, and dichloroethane; ethers such as cyclopentyl methyl ether, tetrahydrofuran, and tetrahydropyran; and the like. Among these, it is preferable to use a compound having a boiling point of 60 to 250° C., and preferably 60 to 150° C., from the viewpoint of handling capability.

When using the method (A), the target liquid crystalline polymer is isolated from a polymerization solution obtained under polymerization conditions described later, and dissolved in an appropriate organic solvent to prepare a solution. The solution is applied to an appropriate support to form a film. The film is dried, heated to a temperature equal to or higher than the temperature at which the liquid crystal polymer shows liquid crystallinity, and then gradually cooled to obtain a liquid crystal state.

Examples of the organic solvent used to dissolve the liquid crystalline polymer include ketones such as acetone, methyl ethyl ketone, methyl isobutyl ketone, cyclopentanone, and cyclohexanone; esters such as butyl acetate and amyl acetate; halogenated hydrocarbons such as dichloromethane, chloroform, and dichloroethane; ethers such as tetrahydrofuran, tetrahydropyran, 1,2-dimethoxyethane, 1,4-dioxane, and cyclopentyl methyl ether; and the like.

As the support, a substrate formed of an organic or inorganic material may be used. Examples of the material for the substrate include polycycloolefins (e.g., Zeonex, Zeonor (registered trademark; manufactured by Zeon Corporation), Arton (registered trademark; manufactured by JSR Corporation), and Apel (registered trademark; manufactured by Mitsui Chemicals Inc.)), polyethylene terephthalate, polycarbonate, polyimide, polyamide, polymethyl methacrylate, polystyrene, polyvinyl chloride, polytetrafluoroethylene, cellulose, cellulose triacetate, polyethersulfone, silicon, glass, calcite, and the like. The substrate may have a tabular shape or a shape having a curved surface. The substrate may optionally include an electrode layer, or have an antireflection function or a reflection function.

The solution of the liquid crystalline polymer may be applied to the support by a known method. Examples of the coating method include a curtain coating method, an extrusion coating method, a roll coating method, a spin coating method, a dip coating method, a bar coating method, a spray coating method, a slide coating method, a print coating method, and the like.

Examples of the organic solvent used for the method (B) include ketones such as acetone, methyl ethyl ketone, methyl isobutyl ketone, cyclopentanone, and cyclohexanone; esters such as butyl acetate and amyl acetate; halogenated hydrocarbons such as dichloromethane, chloroform, and dichloroethane; ethers such as tetrahydrofuran, tetrahydropyran, 1,2-dimethoxyethane, 1,4-dioxane, and cyclopentyl methyl ether; and the like.

The support is not particularly limited. For example, it is possible to use the above support to which the solution of the liquid crystalline polymer may be applied.

When using the method (B), the polymerization solution may be applied to the support by a known method. For example, the polymerization solution may be applied to the support by any of the methods that may be used to apply the solution of the liquid crystalline polymer to the support.

When using the method (B), it is preferable to align the polymerizable liquid crystal compound applied to the support. The polymerizable liquid crystal compound may be aligned by subjecting the support to an alignment process in advance, for example. The support is preferably subjected to the alignment process forming a liquid crystal alignment layer (e.g., polyimide alignment film or polyvinyl alcohol alignment film) on the support, and rubbing the liquid crystal alignment layer, forming an alignment film by obliquely depositing $SiO_2$ on the support, or applying polarized light or non-polarized light to an organic thin film having a functional group that undergoes a photo-dimerization reaction in the molecule or an organic thin film having a functional group that is optically isomerized in the molecule, for example. The polymerizable liquid crystal compound may be polymerized under polymerization conditions described later.

(2) Liquid Crystalline Polymer Obtained by Polymerizing the Polymerizable Liquid Crystal Composition of the Present Invention A liquid crystalline polymer may be easily obtained by polymerizing the polymerizable liquid crystal composition of the present invention in the presence of a polymerization initiator. The resulting liquid crystalline polymer is a cholesteric liquid crystalline polymer. It is preferable to use a polymerizable liquid crystal composition that includes the polymerizable liquid crystal compound, the polymerization initiator (particularly a photoinitiator), and the polymerizable chiral compound, from the viewpoint of ensuring an efficient polymerization reaction. The polymerizable liquid crystal composition is used as described below.

For example, the polymerizable liquid crystal composition of the present invention is applied to a support having an alignment function that is obtained by the above alignment method, and the polymerizable liquid crystal compound included in the polymerizable liquid crystal composition is uniformly aligned while maintaining a cholesteric phase, and polymerized to obtain a liquid crystalline polymer. As the support, the above support may be used.

The alignment state of the polymerizable liquid crystal compound can be easily controlled by utilizing a polyimide thin film that applies a pretilt angle used in a twisted nematic (TN) element or super-twisted nematic (STN) element so that a uniform alignment state can be achieved.

When a liquid crystal composition is caused to come in contact with a support having an alignment function, the liquid crystal compound is aligned on the surface of the support in the alignment direction of the support. Whether the liquid crystal compound is aligned horizontally, obliquely, or vertically with respect to the surface of the support is mainly determined by the alignment process performed on the surface of the support. For example, a polymerizable liquid crystal layer that is aligned almost horizontally with respect to the surface of the support is obtained by providing an alignment film having a very small pretilt angle used for an in-plane switching (IPS) liquid crystal display element.

A polymerizable liquid crystal layer that is tilted to some extent with respect to the surface of the support is obtained by providing an alignment film used for a TN liquid crystal display element on the support. A polymerizable liquid crystal layer that is tilted to a large extent with respect to the surface of the support is obtained by providing an alignment film used for an STN liquid crystal display element on the support.

When the polymerizable liquid crystal composition of the present invention is caused to come in contact with a support having a horizontal alignment function with a pretilt angle, an optically anisotropic article that is obliquely aligned in a state in which the angle uniformly or continuously changes from the surface of the support to the interface with air can be obtained.

A substrate in which areas having different alignment directions are distributed in a pattern can be obtained by applying polarized light or non-polarized light to an organic thin film having a functional group that undergoes a photodimerization reaction in the molecule or an organic thin film having a functional group that is optically isomerized in the molecule (hereinafter referred to as "optical alignment film") (optical alignment method). Specifically, a support provided with an optical alignment film is provided, and light having a wavelength within the absorption band of the optical alignment film is applied to the support to prepare a support that ensures uniform alignment. Light that has a wavelength within the absorption wavelength band of the optical alignment film and differs from the previously applied light (e.g., light that differs in polarization state or irradiation angle and direction from the previously applied light) is applied through a mask to selectively provide an area with an alignment function differing from that of the previously irradiated area.

When the polymerizable liquid crystal composition is caused to come in contact with the support in which areas that differ in alignment function are distributed in a pattern, areas that differ in alignment direction are distributed in a pattern corresponding to the alignment function of the support. A liquid crystalline polymer film having an alignment pattern can be obtained by causing photopolymerization to occur in this state.

When using a support having an approximately horizontal alignment function in which areas that differ in alignment direction are distributed in a pattern, a liquid crystal polymer film that is particularly useful as a retardation film can be obtained.

An alignment pattern may be obtained by rubbing the alignment film with an atomic force microscope (AFM) stylus, or etching the optically anisotropic article, for example. However, it is preferable to use the optical alignment film due to convenience.

The polymerizable liquid crystal composition of the present invention may be applied to the support by a known coating method (e.g., bar coating, spin coating, roll coating, gravure coating, spray coating, die coating, cap coating, or dipping). An organic solvent may be added to the polymerizable liquid crystal composition in order to improve the applicability of the polymerizable liquid crystal composition. In this case, it is preferable to remove the organic solvent by air-drying, drying by heating, drying under reduced pressure, drying by heating under reduced pressure, or the like after applying the polymerizable liquid crystal composition to the support.

After application, it is preferable to cause the liquid crystal compound included in the polymerizable liquid crystal composition to be uniformly aligned in a state in which the cholesteric phase is maintained. Specifically, alignment may be promoted by performing a heat treatment that promotes alignment of the liquid crystal.

For example, the polymerizable liquid crystal composition is applied to the support, and heated to a temperature equal to or higher than the C (crystal phase)-N (nematic phase) transition temperature (hereinafter referred to as "C—N transition temperature") of the liquid crystal composition, so that the polymerizable liquid crystal composition shows a liquid crystal phase or isotropic phase liquid state. The liquid crystal composition is then optionally gradually cooled to obtain a cholesteric phase. In this case, it is preferable to maintain the polymerizable liquid crystal composition at a temperature at which the polymerizable liquid crystal composition shows a liquid crystal phase so that the liquid crystal phase domain is sufficiently grown into a mono-domain.

The polymerizable liquid crystal composition of the present invention may be applied to the support, and maintained for a given time at a temperature within a range in which the polymerizable liquid crystal composition shows a cholesteric phase. The above heat treatment enables preparation of a uniform liquid crystalline polymer film with only a small number of alignment defects as compared with a simple application method. If the temperature is too high, the polymerizable liquid crystal compound may deteriorate due to an undesirable polymerization reaction.

The film is then cooled to the lowest temperature at which the liquid crystal phase does not undergo phase separation (i.e. excessively cooled state), and polymerized at the above temperature in a state in which the liquid crystal phase is aligned to obtain a liquid crystal polymer film having a high degree of alignment and excellent transparency. If the polymerizable liquid crystal composition is cooled to a large extent, the polymerizable liquid crystal composition may undergo phase separation so that crystals may precipitate, or a higher-order liquid crystal phase (e.g., smectic phase) may be produced (i.e., alignment may become impossible).

The polymerizable liquid crystal compound or the polymerizable liquid crystal composition may be polymerized by applying activated energy rays, applying a thermal polymerization method, or the like. It is preferable to polymerize the polymerizable liquid crystal compound or the polymerizable liquid crystal composition by applying activated energy rays since heating is not required (i.e., the reaction proceeds at room temperature). It is preferable to apply light (e.g., ultraviolet rays) from the viewpoint of convenience.

The irradiation temperature is set so that the polymerizable liquid crystal compound or the polymerizable liquid crystal composition can maintain a liquid crystal phase. The irradiation temperature is preferably 30° C. or less in order to avoid a situation in which the polymerizable liquid crystal compound or the polymerizable liquid crystal composition undergoes thermal polymerization. Note that the polymerizable liquid crystal compound or the polymerizable liquid crystal composition normally shows a liquid crystal phase within a range from the C—N transition temperature to the N (nematic phase)-I (isotropic liquid phase) transition temperature (hereinafter abbreviated to "N-I transition temperature") during an increase in temperature. On the other hand, since a thermodynamically nonequilibrium state is maintained during a decrease in temperature, the polymerizable liquid crystal compound or the polymerizable liquid crystal composition may not coagulate at a temperature equal to or lower than the C—N transition temperature to maintain a liquid crystal state. This state is referred to as a "supercooled state". It is considered herein that the polymerizable liquid crystal compound or the polymerizable liquid crystal composition that is in a supercooled state maintains a liquid crystal phase.

The UV dose is normally 1 W/m$^2$ to 10 kW/m$^2$, and preferably 5 W/m$^2$ to 2 kW/m$^2$.

A liquid crystalline polymer film having a plurality of areas that differ in alignment direction can be obtained by polymerizing only a given area of the polymerizable liquid crystal compound or the polymerizable liquid crystal composition by applying ultraviolet rays through a mask, changing the alignment state of the unpolymerized area by applying an electric field, a magnetic field, heat, or the like, and polymerizing the unpolymerized area.

A liquid crystal polymer film having a plurality of areas that differ in alignment direction can also be obtained by limiting the alignment state of the unpolymerized polymerizable liquid crystal compound or the polymerizable liquid crystal composition by applying an electric field, a magnetic field, heat, or the like, and polymerizing only a given area of the polymerizable liquid crystal compound or the polymerizable liquid crystal composition by applying ultraviolet rays through a mask.

A liquid crystal polymer obtained by polymerizing the polymerizable liquid crystal compound or the polymerizable liquid crystal composition may be used after removing the liquid crystal polymer from the support, or may be directly used as an optically anisotropic article without removing the liquid crystal polymer from the support.

The number average molecular weight of the liquid crystal polymer thus obtained is preferably 500 to 500,000, and more preferably 5000 to 300,000. If the number average molecular weight of the liquid crystal polymer is within the above range, the resulting film exhibits high hardness and excellent handling capability. The number average molecular weight of the liquid crystal polymer may be measured by gel permeation chromatography (GPC) using monodisperse polystyrene as a standard (eluant: tetrahydrofuran (THF)).

The liquid crystalline polymer of the present invention is considered to uniformly have a crosslinking point over the entire molecule. Since the liquid crystal polymer is obtained by polymerizing the polymerizable liquid crystal compound of the present invention, the liquid crystal polymer exhibits high crosslinking efficiency and excellent hardness.

Since a liquid crystalline polymer film obtained by polymerizing the polymerizable liquid crystal composition of the present invention is a cholesteric liquid crystal film that has a very high reflectance, the liquid crystal polymer film is suitable as a polarizer for a liquid crystal display element.

It is also possible to stack a plurality of liquid crystalline polymer films by a laminating method to obtain a multilayer polarizer that covers the entire visible light spectrum by appropriately selecting the wavelength of the liquid crystal polymer film (refer to EP0720041).

The liquid crystalline polymer film may also be used as a broad-band polarizer by combining an appropriate compound and appropriate process conditions. In this case, the methods disclosed in WO98/08135, EP0606940, GB2312529, WO96/02016, and the like may be used, for example.

A color filter may be produced using the polymerizable liquid crystal compound or the polymerizable liquid crystal composition. In this case, the desired wavelength may be appropriately obtained by a known coating method.

It is also possible to utilize the thermochromism of the cholesteric liquid crystal. The color of the cholesteric phase changes from red to blue through green when the temperature is adjusted. A given area may be polymerized at a given temperature using a mask.

The liquid crystal polymer of the present invention may be used as a material for an optically anisotropic article such as a retardation film, an alignment film for liquid crystal display elements, a polarizer, a color filter, a low-pass filter, an optical polarization prism, an optical filter, and the like, by utilizing the anisotropy of physical properties (e.g., alignment, refractive index, dielectric constant, and magnetic susceptibility).

4) Optically Anisotropic Article

An optically anisotropic article of the present invention comprises the liquid crystalline polymer of the present invention as a constituting material.

Examples of the optically anisotropic article of the present invention include a retardation film, an alignment film for liquid crystal display elements, a polarizer, a viewing angle enlargement plate, a color filter, a low-pass filter, an optical polarization prism, an optical filter, and the like.

Since the optically anisotropic article of the present invention includes a liquid crystalline polymer obtained by polymerizing the polymerizable liquid crystal compound of the present invention, the optically anisotropic article exhibits uniform and high-quality liquid crystal alignment properties.

EXAMPLES

The present invention is further described below by way of examples. Note that the present invention is not limited to the following examples. Note that the units "parts" and "%" respectively indicate "parts by weight" and "wt %", unless otherwise indicated.

The test methods used are described later. The ratio of the eluants used for column chromatography (i.e., the ratio in the parentheses) is a volume ratio.

Example 1

Synthesis of Polymerizable Liquid Crystal Compound 1 Shown by Formula (I-1)

[Chemical Formula 36]

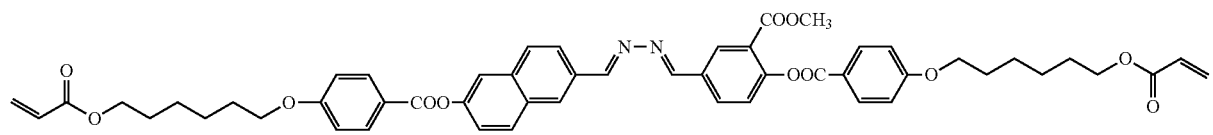

(I-1)

Step 1: Synthesis of Intermediate 1a Shown by Formula (1a)

[Chemical Formula 37]

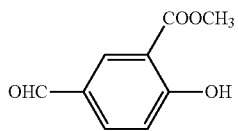

(1a)

In a four-necked reactor equipped with a condenser, a thermometer, and a dropping funnel, 30 g (0.18 mol) of 5-formylsalicylic acid, 29 g (0.9 mol) of methanol, and 4.4 g (0.036 mol) of 4-(dimethylamino)pyridine were dissolved in 400 ml of tetrahydrofuran (THF) in a nitrogen stream. A solution prepared by dissolving 74.6 g (0.36 mol) of N,N-dicyclohexylcarbodiimide in 150 ml of THF was slowly added to the solution at room temperature. After the addition, the mixture was stirred at room temperature for 8 hours.

After completion of the reaction, insoluble components were filtered off from the reaction mixture. The solvent was evaporated from the filtrate under reduced pressure to obtain a yellow oil. The yellow oil was purified by silica gel column chromatography (n-hexane:THF=9:1) to obtain 23.1 g of a white solid intermediate 1a (yield: 71.2%). The structure of the intermediate 1a was identified by $^1$H-NMR.

($^1$H-NMR Data of Intermediate 1a)
$^1$H-NMR (500 MHz, CDCl$_3$, TMS, δ ppm): 11.36 (s, 1H), 9.88 (s, 1H), 8.39 (s, 1H), 8.00 (d, 1H, J=9.0 Hz), 7.11 (d, 1H, J=9.0 Hz), 4.01 (s, 3H)

Step 2: Synthesis of Intermediate 1b Shown by Formula (1b)

[Chemical Formula 38]

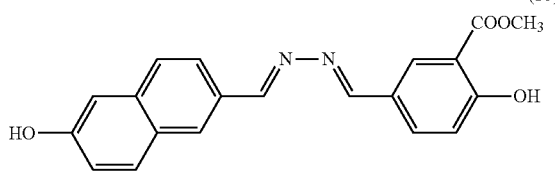

(1b)

In a four-necked reactor equipped with a condenser, a thermometer, and a dropping funnel, 2.78 g (55.5 mmol) of hydrazine monohydrate was dissolved in 100 ml of ethanol in a nitrogen stream. After the addition of 10 g (55.5 mmol) of the intermediate 1a (solid) to the solution at room temperature, the mixture was stirred for 2 hours. After the addition of 9.56 g (55.5 mmol) of 6-hydroxy-2-naphthaldehyde, the mixture was stirred at room temperature for 12 hours.

After completion of the reaction, insoluble components were filtered off from the reaction mixture. The solvent was evaporated from the filtrate under reduced pressure to obtain a yellow solid. The yellow solid was purified by silica gel column chromatography (n-hexane:THF=2:1) to obtain 3.1 g of a yellow solid intermediate 1b (yield: 16.0%). The structure of the intermediate 1b was identified by $^1$H-NMR.

($^1$H-NMR Data of Intermediate 1b)
$^1$H-NMR (500 MHz, THF-d8, TMS, δ ppm): 11.35 (s, 1H), 9.19 (s, 1H), 9.02 (s, 1H), 8.92 (s, 1H), 8.61 (d, 1H, J=2.5 Hz), 8.37-8.29 (m, 3H), 8.07 (d, 1H, J=8.5 Hz), 7.95 (d, 1H, J=8.5 Hz), 7.38-7.32 (m, 3H), 4.26 (s, 3H)

Step 3: Synthesis of Polymerizable Liquid Crystal Compound 1

In a four-necked reactor equipped with a condenser, a thermometer, and a dropping funnel, 6.29 g (21.5 mmol) of 4-(6-acryloyl-n-hexyloxy)benzoic acid (manufactured by DKSH Japan K.K.) and 3.12 g (24.1 mmol) of N,N-diisopropylethylamine were dissolved in 50 ml of THF in a nitrogen stream. 2.47 g (21.6 mmol) of methanesulfonyl chloride was slowly added to the solution in an ice bath. After the addition, the mixture was stirred at room temperature for 1 hour. 0.26 g (2.1 mmol) of 4-(dimethylamino)pyridine and 3.0 g (8.6 mmol) of the intermediate 1b were added to the solution at room temperature in an ice bath. 2.23 g (17.3 mmol) of N,N-diisopropylethylamine was slowly added to the solution. After the addition, the mixture was stirred at room temperature for 2 hours.

After completion of the reaction, 100 g of methanol was slowly added dropwise to the reaction mixture to precipitate a solid. The solid thus precipitated was collected by filtration to obtain a light yellow solid. The light yellow solid was purified by silica gel column chromatography (toluene:ethyl acetate=9:1, then changed to toluene:ethyl acetate=8:2) to obtain 4.8 g of a polymerizable liquid crystal compound 1 (light yellow solid) shown by the formula (I-1) (yield: 62.2%). The structure of the polymerizable liquid crystal compound 1 was identified by $^1$H-NMR.

($^1$H-NMR Data of Polymerizable Liquid Crystal Compound 1)
$^1$H-NMR (500 MHz, CDCl$_3$, TMS, δ ppm): 8.85 (s, 1H), 8.75 (s, 1H), 8.52 (s, 1H), 8.21-8.14 (m, 7H), 7.99 (d, 1H, J=8.5 Hz), 7.90 (d, 1H, J=8.5 Hz), 7.72 (d, 1H, J=2.0 Hz), 7.42 (dd, 1H, J=2.0 Hz, J=9.0 Hz), 7.35 (d, 1H, J=8.5 Hz), 7.00 (m, 4H), 6.42 (dd, 2H, J=1.5 Hz, J=17.5 Hz), 6.14 (dd, 2H, J=10.5 Hz, J=17.5 Hz), 5.84 (dd, 2H, J=1.5 Hz, J=10.5 Hz), 4.19 (t, 4H, J=6.5 Hz), 4.08-4.05 (m, 4H), 3.80 (s, 3H), 1.89-1.83 (m, 4H), 1.77-1.71 (m, 4H), 1.58-1.45 (m, 8H)

Example 2

Synthesis of Polymerizable Liquid Crystal Compound 2 Shown by Formula (I-2)

[Chemical Formula 39]

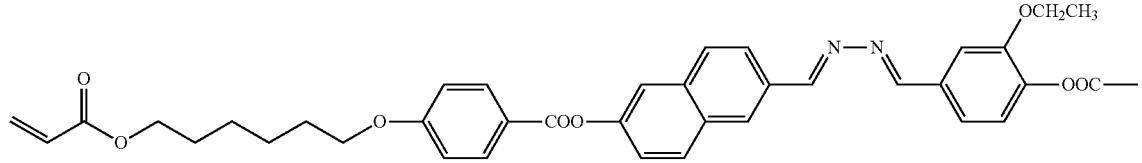

(I-2)

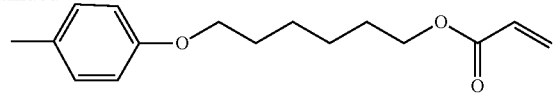

Step 1: Synthesis of Intermediate 2c Shown by Formula (2c)

[Chemical Formula 40]

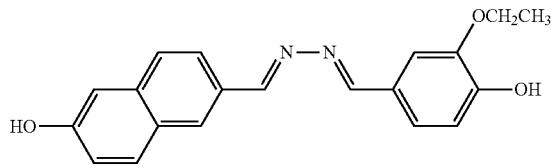

(2c)

In a four-necked reactor equipped with a condenser, a thermometer, and a dropping funnel, 6.0 g (0.12 mol) of hydrazine monohydrate was dissolved in 500 ml of ethanol in a nitrogen stream. After the addition of 20 g (0.12 mol) of 3-ethoxy-4-hydroxybenzaldehyde (ethyl vanillin) (solid) to the solution at room temperature, the mixture was stirred at room temperature for 2 hours. After the addition of 20.66 g (0.12 mol) of 6-hydroxy-2-naphthaldehyde, the mixture was stirred at room temperature for 12 hours.

After completion of the reaction, insoluble components were filtered off from the reaction mixture. The solvent was evaporated from the filtrate under reduced pressure to obtain a yellow solid. The yellow solid was purified by silica gel column chromatography (n-hexane:THF=2:1) to obtain 5.2 g of a yellow solid intermediate 2c (yield: 13.0%). The structure of the intermediate 2c was identified by $^1$H-NMR.

($^1$H-NMR Data of Intermediate 2c)

$^1$H-NMR (500 MHz, THF-d8, TMS, δ ppm): 8.82 (s, 1H), 8.70 (s, 1H), 8.55 (s, 1H), 8.22 (s, 1H), 8.21-8.19 (m, 2H), 7.97 (d, 1H, J=8.5 Hz), 7.84 (d, 1H, J=8.5 Hz), 7.73 (d, 1H, J=1.5 Hz), 7.41 (dd, 1H, J=1.5 Hz, J=8.5 Hz), 7.28-7.25 (m, 2H), 7.02 (d, 1H, J=8.5 Hz), 4.35 (q, 2H, J=6.5 Hz, J=13.5 Hz), 1.64 (t, 3H, J=7.0 Hz)

Step 2: Synthesis of Polymerizable Liquid Crystal Compound 2

In a four-necked reactor equipped with a condenser, a thermometer, and a dropping funnel, 6.29 g (21.5 mmol) of 4-(6-acryloyl-n-hexyloxy)benzoic acid (manufactured by DKSH Japan K.K.) and 3.12 g (24.1 mmol) of N,N-diisopropylethylamine were dissolved in 50 ml of THF in a nitrogen stream. 2.47 g (21.6 mmol) of methanesulfonyl chloride was slowly added to the solution in a water bath. After the addition, the mixture was stirred at room temperature for 1 hour. 0.26 g (2.1 mmol) of 4-(dimethylamino)pyridine and 2.88 g (8.6 mmol) of the intermediate 2c were added to the solution at room temperature in an ice bath. 2.23 g (17.3 mmol) of N,N-diisopropylethylamine was slowly added to the solution. After the addition, the mixture was stirred at room temperature for 2 hours.

After completion of the reaction, 100 g of methanol was slowly added dropwise to the reaction mixture to precipitate a solid. The solid thus precipitated was collected by filtration to obtain a light yellow solid. The light yellow solid was purified by silica gel column chromatography (toluene:ethyl acetate=9:1, then changed to toluene:ethyl acetate=8:2) to obtain 3.9 g of a polymerizable liquid crystal compound 2 (light yellow, solid) shown by the formula (I-2) (yield: 51.4%). The structure of the polymerizable liquid crystal compound 2 was identified by $^1$H-NMR.

($^1$H-NMR Data of Polymerizable Liquid Crystal Compound 2)

$^1$H-NMR (500 MHz, CDCl$_3$, TMS, δ ppm):8.83 (s, 1H), 8.70 (s, 1H), 8.21-8.13 (m, 6H), 7.98 (d, 1H, J=9.0 Hz), 7.89 (d, 1H, J=9.0 Hz), 7.72 (d, 1H, J=2.0 Hz), 7.65 (d, 1H, J=1.5 Hz), 7.42 (dd, 1H, J=2.0 Hz, J=9.0 Hz), 7.38 (dd, 1H, J=1.5 Hz, J=9.0 Hz), 7.25 (d, 1H, J=9.0 Hz), 7.01-6.97 (m, 4H), 6.42 (d, 2H, J=16.0 Hz), 6.14 (dd, 2H, J=10.5 Hz, J=16.0 Hz), 5.84 (d, 2H, J=10.5 Hz), 4.21-4.15 (m, 6H), 4.08-4.05 (m, 4H), 1.89-1.83 (m, 4H), 1.77-1.71 (m, 4H), 1.59-1.45 (m, 8H), 1.35 (t, 3H, J=7.0 Hz)

(Evaluation of Polymerizable Liquid Crystal Compound)

(1) Measurement of Phase Transition Temperature 10 mg of the polymerizable liquid crystal compound (the polymerizable liquid crystal compounds 1 and 2 obtained in Examples 1 and 2, and a polymerizable liquid crystal compound shown by the following formula (3) ("LC242" manufactured by BASF) (Comparative Example 1) (hereinafter referred to as "polymerizable liquid crystal compound 3")) was weighed, and placed between two glass substrates provided with a rubbed polyimide alignment film.

[Chemical Formula 41]

(3)

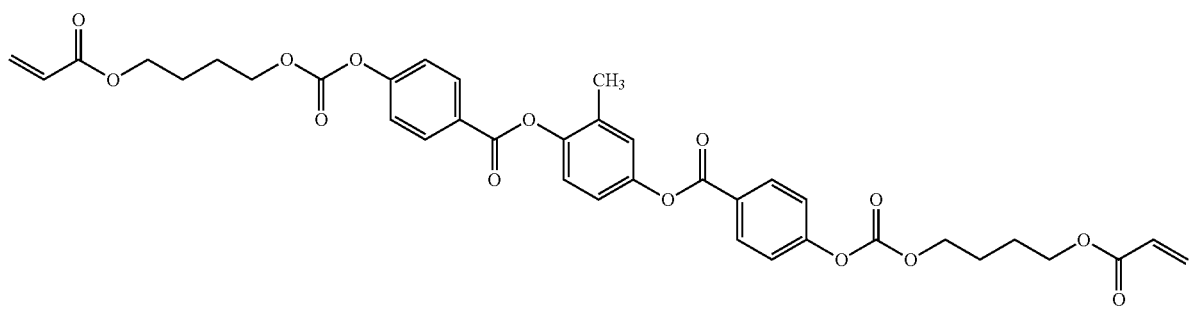

The substrates were heated from 30° C. to 300° C. on a hot plate, and then cooled to 30° C. A change in structure during a change in temperature was observed using a polarizing optical microscope ("ECLIPSE LV100POL" manufactured by Nikon Corporation) to determine the phase transition temperature. The phase transition temperature thus determined is shown in Table 1.

In Table 1, "C" indicates "Crystal", "N" indicates "Nematic", and "I" indicates "Isotropic". "Crystal" indicates that the test compound was in a solid phase, "Nematic" indicates that the test compound was in a nematic liquid crystal phase, and "Isotropic" indicates that the test compound was in an isotropic liquid phase.

(2) Formation of Cholesteric Phase 100 parts of the polymerizable liquid crystal compound (1 to 3) was dissolved in 153 parts of cyclopentanone. After the addition of 3.3 parts of a photoinitiator ("Irgacure 379" manufactured by Ciba Specialty Chemicals Co., Ltd.), 6 parts of a polymerizable chiral compound (compound shown by the formula (X)), and 11.6 parts of a surfactant ("KH-40" manufactured by AGC Seimi Chemical Co., Ltd.; 1 wt % cyclopentanone solution), the components were homogenously dissolved to prepare a polymerizable liquid crystal composition solution.

The polymerizable liquid crystal composition solution thus prepared was applied to a glass substrate provided with a rubbed polyimide alignment film using a bar coater ("SA-203" manufactured by Tester Sangyo Co., Ltd., Rod No. 8, shaft diameter: 12.7 mm). After drying the resulting film at 100° C. for 3 minutes on a hot plate, ultraviolet rays (1000 mJ/cm$^2$) were applied to the film from a mercury lamp to obtain a cured liquid crystal polymer film having a thickness of 4 μm.

The transmission spectrum of the cured film was measured using a spectrophotometer ("MCPD-3000" manufactured by Otsuka Electronics Co., Ltd.). A selective reflection region (i.e., a region in which the transmittance was about 50%) was observed when a cholesteric phase was formed. The bandwidth was about 50 to 100 nm. A case where a cholesteric phase was formed is indicated by "Formed", and a case where a cholesteric phase was not formed is indicated by "Not formed". The evaluation results are shown in Table 1.

When forming the cured film of the compound, the mutual solubility of the compound at 23° C. was evaluated by naked eye observation. A case where turbidity was not observed was evaluated as "Good", and a case where turbidity was observed was evaluated as "Bad". The evaluation results are shown in Table 1.

The solubility of the compound at 60° C. was evaluated when preparing a solution having a compound concentration of 40 wt %. The evaluation results are shown in Table 1. In Table 1, a case where the compound was dissolved in cyclopentanone is indicated by "Good", and a case where the compound was not dissolved in cyclopentanone is indicated by "Bad".

(3) Measurement of Optical Anisotropy (Value Δn)

100 parts of the polymerizable liquid crystal compound (1 to 3) was dissolved in 233 parts of cyclopentanone. 2.7 parts of a photoinitiator ("Irgacure 907" manufactured by Ciba Specialty Chemicals Co., Ltd.) was homogenously dissolved in the solution. The resulting solution was applied to a glass substrate provided with a rubbed polyimide alignment film using a bar coater ("SA-203" manufactured by Tester Sangyo Co., Ltd., Rod No. 4, shaft diameter: 12.7 mm). After drying the resulting film at 100° C. for 5 minutes on a hot plate, ultraviolet rays (1000 mJ/cm$^2$) were applied to the film from a mercury lamp to obtain a cured polymer film having a thickness of 4 μm.

The extinction position (θ) of the cured film was measured using an optical microscope ("ECLIPSE E600POL (transmission/reflection type)" manufactured by Nikon Corporation, equipped with a sensitive tint plate, a λ/4 wave plate, a Sénarmont compensator, and a GIF filter (546 nm). The retardation (Re) was calculated by "Re=λ(546 nm)×θ/180". The value Δn was calculated by "Δn=Re/d" (where, d is the thickness of the liquid crystal layer). The calculation results are shown in Table 1.

TABLE 1

| | Polymerizable liquid crystal compound | Phase transition temperature | Liquid crystallinity temperature range | Solubility | Cholesteric phase | Mutual solubility | Δn |
|---|---|---|---|---|---|---|---|
| Example 1 | 1 | C ⇌ N (90° C. / 30° C. or less) → I (300° C. or more) | 210° C. or more | Good | Formed | Good | 0.254 |
| Example 2 | 2 | C ⇌ N (95° C. / 30° C. or less) → I (300° C. or more) | 205° C. or more | Good | Formed | Good | 0.291 |
| Comparative Example 1 | 3 | C →*1 N (60° C.) → I (123° C.) | 63° C. | Good | Formed | Good | 0.142 |

*1: Cooled to 30° C. in an isotropic state.

The following items were confirmed from the test results shown in Table 1.

Specifically, the polymerizable liquid crystal compounds 1 and 2 exhibited high solubility in the solvent, and had excellent mutual solubility with the additives (e.g., polymerization initiator and polymerizable chiral compound) (i.e., exhibited excellent handling capability).

The cured polymer films obtained from the polymerizable liquid crystal compounds 1 and 2 showed excellent liquid crystallinity over a wide temperature range, and formed a cholesteric phase. The resulting cured film was a liquid crystal film that exhibited excellent optical anisotropy (Δn).

On the other hand, the polymerizable liquid crystal compound 3 of Comparative Example 1 that did not have the structure according to the present invention showed liquid crystallinity within a narrow temperature range.

INDUSTRIAL APPLICABILITY

Since the liquid crystalline polymer according to the present invention exhibits excellent alignment properties and high optical anisotropy (Δn), the liquid crystalline polymer is useful as a material for forming an optically anisotropic article such as a retardation film, an alignment film for liquid crystal display elements, a polarizer, a viewing angle enlargement plate, a color filter, a low-pass filter, an optical polarization prism, and an optical filter.

The invention claimed is:

1. A polymerizable liquid crystal compound shown by the following formula (1),

[Chemical Formula 1]

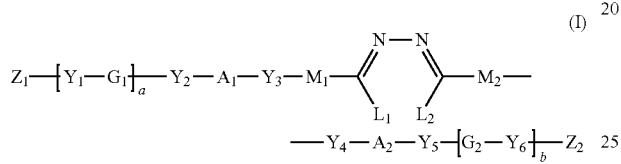

wherein $Y_1$ to $Y_6$ individually represent a single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—, R$^1$ represents a hydrogen atom or an alkyl group having 1 to 6 carbon atoms, $G_1$ and $G_2$ individually represent a substituted or unsubstituted divalent aliphatic group having 1 to 20 carbon atoms that may include —O—, —S—, —O—C(=O)—, —C(=O)—O—, —O—C(=O)—O—, —NR$^2$—C(=O)—, —C(=O)—NR$^2$—, —NR$^2$—, or —C(=O)— (excluding a case where the aliphatic group includes two or more adjacent —O— or —S—), R$^2$ represents a hydrogen atom or an alkyl group having 1 to 6 carbon atoms, $Z_1$ and $Z_2$ individually represent an alkenyl group having 2 to 10 carbon atoms that may be substituted with a halogen atom, $A_1$ and $A_2$ individually represent a divalent organic group A having 1 to 30 carbon atoms, $M_1$ and $M_2$ individually represent a substituted or unsubstituted 2,6-naphthylene group or a substituted or unsubstituted 1,4-phenylene group, provided that at least one of $M_1$ and $M_2$ represents a substituted or unsubstituted 2,6-naphthylene group, $L_1$ and $L_2$ individually represent a hydrogen atom or an alkyl group having 1 to 6 carbon atoms, and a and b are individually 0 or 1.

2. The polymerizable liquid crystal compound according to claim 1, wherein $A_1$ and $A_2$ individually represent a substituted or unsubstituted phenylene group, a substituted or unsubstituted biphenylene group, or a substituted or unsubstituted naphthylene group.

3. The polymerizable liquid crystal compound according to claim 1, wherein $Z_1$ and $Z_2$ individually represent CH$_2$=CH—, CH$_2$=C(CH$_3$)—, CH$_2$=CH—CH$_2$—, CH$_3$—CH=CH—, CH$_2$=CH—CH$_2$—CH$_2$—, CH$_2$=C(CH$_3$)—CH$_2$—CH$_2$—, (CH$_3$)$_2$C=CH—CH$_2$—, (CH$_3$)$_2$C=CH—CH$_2$—CH$_2$—, CH$_2$=C(Cl)—, CH$_2$=C(CH$_3$)—CH$_2$—, or CH$_3$—CH=CH—CH$_2$—.

4. The polymerizable liquid crystal compound according to claim 1, wherein $M_1$ represents a substituted or unsubstituted 2,6-naphthylene group, and $M_2$ represents a substituted or unsubstituted 1,4-phenylene group.

5. The polymerizable liquid crystal compound according to claim 1, wherein $Y_1$ to $Y_6$ individually represent —O—, —C(=O)—O—, or —O—C(=O)—, $G_1$ and $G_2$ individually represent —(CH$_2$)$_6$— or —(CH$_2$)$_4$— that may include —O—, —C(=O)—O—, or —O—C(=O)—, $Z_1$ and $Z_2$ individually represent CH$_2$=CH—, CH$_2$=C(CH$_3$)—, or CH$_2$=C(Cl)—, $A_1$ and $A_2$ individually represent one of the groups shown by the following formulas,

[Chemical Formula 2]

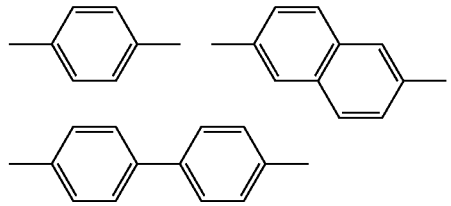

$M_1$ represents a substituted or unsubstituted 2,6-naphthylene group, and $M_2$ represents a substituted or unsubstituted 1,4-phenylene group.

6. The polymerizable liquid crystal compound according to claim 1, wherein $Y_1$ to $Y_6$ individually represent —O—, —C(=O)—O—, or —O—C(=O)—, $G_1$ and $G_2$ individually represent —(CH$_2$)$_6$— or —(CH$_2$)$_4$—, $Z_1$ and $Z_2$ individually represent CH$_2$=CH— or CH$_2$=C(CH$_3$)—, $A_1$ and $A_2$ represent by the group shown by the following formula,

[Chemical Formula 3]

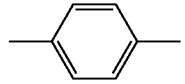

$M_1$ represents a substituted or unsubstituted 2,6-naphthylene group, and $M_2$ represents a substituted or unsubstituted 1,4-phenylene group.

7. The polymerizable liquid crystal compound according to claim 1, wherein $Y_1$ to $Y_6$ individually represent —O—, —C(=O)—O—, or —O—C(=O)—, $G_1$ and $G_2$ individually represent —(CH$_2$)$_6$— or —(CH$_2$)$_4$—, $Z_1$ and $Z_2$ represent CH$_2$=CH—, $A_1$ and $A_2$ represent the group shown by the following formula,

[Chemical Formula 4]

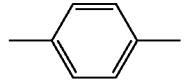

$M_1$ represents a 2,6-naphthylene group, and $M_2$ represents a substituted or unsubstituted 1,4-phenylene group.

8. The polymerizable liquid crystal compound according to claim 1, wherein $L_1$ and $L_2$ represent a hydrogen atom.

9. A polymerizable liquid crystal composition comprising the polymerizable liquid crystal compound according to claim 1, and a polymerizable chiral compound that is polymerizable with the polymerizable liquid crystal compound.

10. A liquid crystalline polymer obtained by polymerizing the polymerizable liquid crystal compound according to claim 1.

11. An optically anisotropic article comprising the liquid crystalline polymer according to claim 10 as a constituting material.

12. The polymerizable liquid crystal compound according to claim 3, wherein $M_1$ represents a substituted or unsubstituted 2,6-naphthylene group, and $M_2$ represents a substituted or unsubstituted 1,4-phenylene group.

13. A polymerizable liquid crystal composition comprising the polymerizable liquid crystal compound according to claim 3, and a polymerizable chiral compound that is polymerizable with the polymerizable liquid crystal compound.

14. A polymerizable liquid crystal composition comprising the polymerizable liquid crystal compound according to claim 4, and a polymerizable chiral compound that is polymerizable with the polymerizable liquid crystal compound.

15. A polymerizable liquid crystal composition comprising the polymerizable liquid crystal compound according to claim 5, and a polymerizable chiral compound that is polymerizable with the polymerizable liquid crystal compound.

16. A liquid crystalline polymer obtained by polymerizing the polymerizable liquid crystal compound according to claim 3.

17. A liquid crystalline polymer obtained by polymerizing the polymerizable liquid crystal compound according to claim 4.

18. A liquid crystalline polymer obtained by polymerizing the polymerizable liquid crystal compound according to claim 5.

19. A liquid crystalline polymer obtained by polymerizing the polymerizable liquid crystal compound according to claim 9.

20. An optically anisotropic article comprising the liquid crystalline polymer according to claim 16 as a constituting material.

21. An optically anisotropic article comprising the liquid crystalline polymer according to claim 17 as a constituting material.

22. An optically anisotropic article comprising the liquid crystalline polymer according to claim 18 as a constituting material.

23. An optically anisotropic article comprising the liquid crystalline polymer according to claim 19 as a constituting material.

* * * * *